(12) United States Patent
Hovland et al.

(10) Patent No.: US 6,964,643 B2
(45) Date of Patent: *Nov. 15, 2005

(54) DEVICES AND METHODS FOR TREATMENT OF INCONTINENCE

(75) Inventors: Claire T. Hovland, Andover, MN (US); Curtis E. Olson, St. Paul, MN (US); Jerome H. Abrams, St. Paul, MN (US); Paul J. Robinson, Mahtomedi, MN (US); Philip A. Messina, St. Paul, MN (US)

(73) Assignee: NuGyn, Inc., Spring Lake Park, MN (US)

( * ) Notice: Subject to any disclaimer, the term of this patent is extended or adjusted under 35 U.S.C. 154(b) by 38 days.

This patent is subject to a terminal disclaimer.

(21) Appl. No.: 10/077,678

(22) Filed: Feb. 15, 2002

(65) Prior Publication Data

US 2002/0120219 A1 Aug. 29, 2002

Related U.S. Application Data

(63) Continuation-in-part of application No. 09/442,803, filed on Nov. 18, 1999, now Pat. No. 6,464,653.
(60) Provisional application No. 60/269,260, filed on Feb. 16, 2001, provisional application No. 60/158,257, filed on Oct. 6, 1999, and provisional application No. 60/108,959, filed on Nov. 18, 1998.

(51) Int. Cl.$^7$ .............................................. A61H 23/02
(52) U.S. Cl. ............................. 601/6; 601/9; 604/315
(58) Field of Search ............................. 601/6, 7, 9, 10; 128/885, 886; 604/313, 315

(56) References Cited

U.S. PATENT DOCUMENTS

| | | | |
|---|---|---|---|
| 882,532 A | 3/1908 | McCall | |
| 1,704,960 A | 3/1929 | Ackerman | |
| 1,730,535 A | 10/1929 | Rudolph | |
| 1,762,692 A | 6/1930 | Lair | |

(Continued)

FOREIGN PATENT DOCUMENTS

| | | | | |
|---|---|---|---|---|
| DE | 3426225 A1 | 1/1986 | | |
| EP | 0 148 586 A1 | 7/1985 | | |
| GB | 392847 A | * | 5/1933 | .................. 601/21 |
| JP | 354115951 A | * | 9/1979 | |
| JP | 403162870 A | * | 7/1991 | |
| WO | WO 00/28939 | 5/2000 | | |
| WO | WO 01/72238 | 10/2001 | | |

OTHER PUBLICATIONS

Shafik, A., Study of the Response of the Urinary Bladder to Stimulation of the Cervix Uteri and Clitoris—The 'Genitovesical Reflex': An Experimental Study, Abstract, Int Urogynecol J 1995 6:41–46, 1995.

(Continued)

Primary Examiner—Danton DeMille
(74) Attorney, Agent, or Firm—Dicke, Billig & Czaja, PLLC

(57) ABSTRACT

Therapeutic devices and methods according to embodiments of the invention alleviate e.g. urinary incontinence in female and male patients. Suction or vacuum, for example, is applied to the genital region, clitoris or clitoral region, the external urethral orifice, and/or other designated areas, e.g. physically stimulating the sacral/pudendal nerves and/or nerve roots and alleviating incontinence. Such embodiments also can encourage or cause clitoral engorgement, or otherwise promote blood flow in the genital region. Vacuum or suction applied to e.g. the clitoris creates a negative pressure in the clitoris that is lower than the systolic blood pressure, tending to promote engorgement of the clitoris with blood. Aspects of the invention are applicable not only to treatment of urinary and fecal incontinence, but also to the treatment of female sexual dysfunction. Aspects of the invention are also applicable to treatment of male incontinence and male erectile dysfunction.

5 Claims, 20 Drawing Sheets

U.S. PATENT DOCUMENTS

| | | |
|---|---|---|
| 1,858,209 A | 5/1932 | Lang |
| 1,861,924 A | 6/1932 | Karlstrom et al. |
| 1,882,040 A | 10/1932 | Roehm |
| 2,112,646 A | 3/1938 | Biederman |
| 2,314,590 A | 3/1943 | McCarty |
| 2,571,398 A * | 10/1951 | Wheeler .................. 601/9 |
| 2,597,966 A | 5/1952 | Adler |
| 2,626,601 A | 1/1953 | Riley |
| 2,655,145 A * | 10/1953 | Heger .................. 601/17 |
| 3,114,916 A | 12/1963 | Hadley |
| 3,236,231 A | 2/1966 | Schneider et al. |
| 3,362,401 A | 1/1968 | Katz |
| 3,382,867 A | 5/1968 | Reaves |
| 3,396,720 A * | 8/1968 | Ohkubo .................. 601/6 |
| 3,504,665 A | 4/1970 | Bakunin, et al. |
| 3,626,931 A | 12/1971 | Bysakh |
| 3,631,853 A | 1/1972 | Burdette, Jr. |
| 3,744,486 A | 7/1973 | Wilson |
| 3,763,854 A | 10/1973 | Welch |
| 3,841,322 A | 10/1974 | Spelio |
| 3,841,323 A | 10/1974 | Stoughton |
| 3,906,940 A | 9/1975 | Kawada |
| 4,003,373 A | 1/1977 | Spelio |
| 4,033,338 A | 7/1977 | Igwebike |
| 4,111,192 A | 9/1978 | Wu |
| 4,215,679 A | 8/1980 | Rustin |
| 4,428,368 A | 1/1984 | Torii |
| 4,531,939 A | 7/1985 | Izumi |
| 4,641,638 A | 2/1987 | Perry |
| 4,718,411 A | 1/1988 | Stewart |
| 4,729,368 A | 3/1988 | Guitay |
| 4,748,973 A | 6/1988 | Cho |
| 4,754,748 A | 7/1988 | Antowski |
| 4,771,779 A | 9/1988 | Tanagho et al. |
| 4,790,296 A | 12/1988 | Segal |
| 4,836,192 A | 6/1989 | Abbate |
| 5,020,522 A | 6/1991 | Stewart |
| D320,087 S | 9/1991 | Sholzberg |
| 5,243,968 A | 9/1993 | Byun |
| 5,336,158 A | 8/1994 | Huggins et al. |
| 5,421,808 A | 6/1995 | Osbon et al. |
| 5,454,778 A | 10/1995 | Liaskos |
| 5,462,514 A | 10/1995 | Harris |
| 5,470,303 A | 11/1995 | Leonard et al. |
| D368,140 S | 3/1996 | Hopper |
| 5,501,650 A | 3/1996 | Gellert |
| 5,573,499 A | 11/1996 | McAllister |
| D376,650 S | 12/1996 | Kain |
| D378,418 S | 3/1997 | Bowker et al. |
| 5,636,643 A | 6/1997 | Argenta et al. |
| 5,681,026 A | 10/1997 | Durand |
| 5,693,002 A | 12/1997 | Tucker et al. |
| 5,695,445 A | 12/1997 | Khouri |
| 5,725,473 A | 3/1998 | Taylor |
| 5,755,236 A | 5/1998 | Dann et al. |
| 5,782,621 A | 7/1998 | Harris |
| 5,877,216 A | 3/1999 | Place et al. |
| 5,885,204 A | 3/1999 | Vergano |
| 5,895,349 A | 4/1999 | Tihon |
| 5,897,512 A | 4/1999 | Zagame |
| 6,015,393 A | 1/2000 | Hovland et al. |
| 6,017,320 A | 1/2000 | Bleeker et al. |
| 6,030,318 A | 2/2000 | Howard |
| 6,030,338 A * | 2/2000 | Benderev .................. 600/30 |
| 6,042,537 A | 3/2000 | Kaiser |
| 6,055,456 A | 4/2000 | Gerber |
| 6,086,549 A | 7/2000 | Neese et al. |
| 6,099,463 A | 8/2000 | Hockhalter |
| 6,169,914 B1 | 1/2001 | Hovland et al. |
| D443,057 S | 5/2001 | Hovland et al. |
| 6,251,076 B1 | 6/2001 | Hovland et al. |
| D449,690 S | 10/2001 | Hovland et al. |

OTHER PUBLICATIONS

"A Study to Evaluate the Safety and Effectiveness of the UroSurge Percutaneous SANS (Stoller Afferent Nerve Stimulator) Device in Treating Patients with Documented Urinary Urgency/Frequency", Aug. 1998, pp. 1–7.

"Nerve stimulation: The future of incontinence Tx?", *Urology Times*, Sep. 1998, pp. 1–4.

"Urinary Incontinence in Adults", National Institutes of Health Consensus Development Conference Statement, Oct. 3–5, 1998, <http://text.nlm.nih.gov/nih/cdc/www/71txt.htm>, pp. 1–20.

"Interstim Therapy for Urinary Control", Medtronic, Inc., 1999.

Frank V. Lefevre, M.D., "Sacral Nerve Stimulation for the Treatment of Refractory Urge Incontinence", Blue Cross and Blue Shield Association, Mar. 2000, pp. 1–28.

"Sacral Nerve Stimulation for Urinary Control Effective Treatment Option", Doctor's Guide to Medical News, Jul. 5, 2000, <http://www.pslgroup.com/dg/1D89D6.htm>, pp. 1–2.

Lefevre, Frank V., M.D., "Sacral Nerve Stimulation for the Treatment of Urinary Urgency/Frequency in Adults", Blue Cross and Blue Shield Association, Aug. 2000, pp. 1–24.

Sacral Nerve Stimulation for Treatment of Urgency Incontinence,: Medicare Coverage Policy—Decisions, Decision Memorandum # CAG–00058, Jun. 29, 2001.

"About Disease", Incontinence Knowledge Center, <www.incontinencenet.org/About/About_Disease.htm>, Jul. 16, 2001, Sections 1–8.

Fall, Magnus, Review of "Percutaneous afferent neuromodulation for the refractory overactive bladder: Results of a multicenter study", <www.incontinencenet.org/lrs/issue4/frameset3 /reviews/Fall.htm>, Nov. 26, 2001.

Levin, R., "The physiology of sexual function in women," Clinical Obstetr Gyn, 7:213, 1980.

Diederichs, W., et al., "Clitoral response to cavernous nerve stimulation in dogs," International Journal of Impotence Research, 3:7, 1991.

Wagner, G., "Aspects of Genital Physiology and Pathology," Seminars in Neurology, 12:87, 1992.

Levin, R., "The mechanisms of human female sexual arousal," Annual Review of Sex Research, 3:1, 1992, abstract.

Schiavi, R., et al., "The biology of sexual function," Psychiatric Clinics of North America, 18:7, Mar. 1995.

Park, K., et al., "Vasculogenic female sexual dysfunction: The hemodynamic basis for vaginal engorgement insufficiency and clitoral erectile insufficiency," International Journal of Impotence Research (1997) 9, 27–37.

Burnett, A., et al., "Immunohistochemical Decription of Nitric Oxide Synthase Isoforms in Human Clitoris," Journal of Urology, vol. 158, 75–78, Jul. 1997.

Goldstein, I., et al., "Vasculogenic female sexual dsfunction: vaginal engorgement and clitoral erectile insufficiency syndromes," International Journal of Impotence Research (1998) 10, Suppl. 2, S84–S90.

Wen, C., et al., "Atherosclerotic vascular disease of the iliohypogastric pudendal bed in females," International Journal of Impotence Research 10:S64, 1998, abstract.

http://sextoy.com/vibrat/pleaser/html, Suckers–sextoys that such the clitoris or nipples, Nov. 15, 1999.

Kohn, I., et al., "Female sexual dysfunction, What is known and what remains to be determined," Contemporary Urology, Sep. 1999, vol. 11, No. 9, 54–72.

Appendix M., Touch II™ Vacuum Erection System Promotional Material, prior to 11–1999.

"Sexual responses of women, dysmenorrhea, and premenstrual tension," Obstetrics and Gynecology, Ch. 8, pp. 97–108, prior to 11–1999.

\* cited by examiner

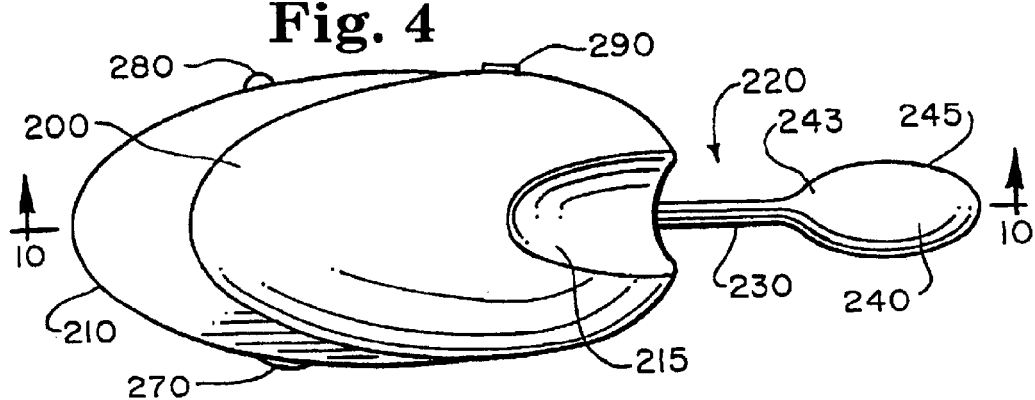
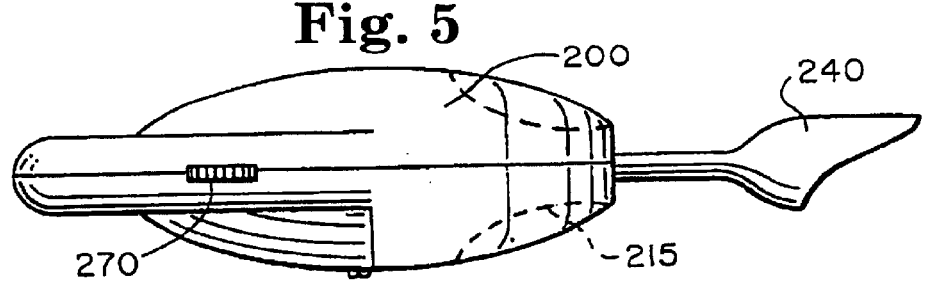
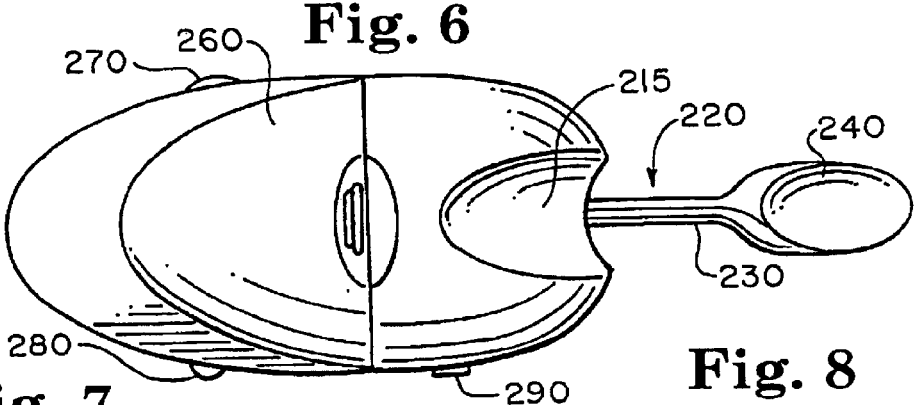
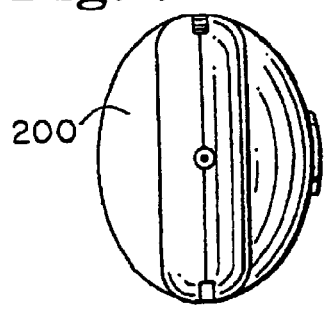
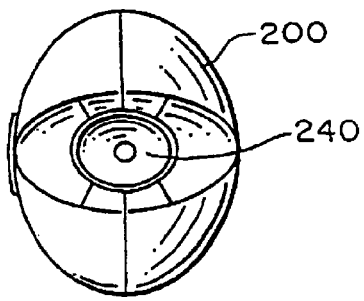

Fig. 31

CHANGES IN SENSATION

| AFTER USING THE DEVICE | WOMEN WITH FSAD(%) | WOMEN WITHOUT FSAD(%) |
|---|---|---|
| MORE THAN BEFORE | 100% | 43% |
| LESS THAN BEFORE | 0% | 0% |
| SAME AS BEFORE | 0% | 57% |
| n= | 7 | 7 |

CHANGES IN ABILITY TO ACHIEVE ORGASM

| AFTER USING THE DEVICE | WOMEN WITH FSAD(%) | WOMEN WITHOUT FSAD(%) |
|---|---|---|
| MORE THAN BEFORE | 57% | 0% |
| LESS THAN BEFORE | 0% | 0% |
| SAME AS BEFORE | 43% | 100% |
| n= | 7 | 7 |

CHANGES IN SEXUAL SATIFACATION

| AFTER USING THE DEVICE | WOMEN WITH FSAD(%) | WOMEN WITHOUT FSAD(%) |
|---|---|---|
| MORE THAN BEFORE | 86% | 14% |
| LESS THAN BEFORE | 0% | 0% |
| SAME AS BEFORE | 14% | 86% |
| n= | 7 | 7 |

CHANGES IN LUBRICATION

| AFTER USING THE DEVICE | WOMEN WITH FSAD(%) | WOMEN WITHOUT FSAD(%) |
|---|---|---|
| MORE THAN BEFORE | 86% | 29% |
| LESS THAN BEFORE | 0% | 0% |
| SAME AS BEFORE | 14% | 57% |
| I COULDN'T TELL, PARTNER YES | 0% | 14% |
| n= | 7 | 7 |

Fig. 32

| ABILITY TO CONTROL BLADDER | WOMEN WITH FREQUENCY/URGE INCONTINENCE |
|---|---|
| MORE THAN BEFORE | 100% |
| LESS THAN BEFORE | 0% |
| SAME AS BEFORE | 0% |
| n= | 3 |

DEVICES AND METHODS FOR TREATMENT OF INCONTINENCE

CROSS-REFERENCE TO RELATED APPLICATIONS

This application is a Continuation-In-Part of U.S. patent application Ser. No. 09/442,803, filed Nov. 18, 1999 now U.S. Pat. No. 6,464,653, which is incorporated herein by reference; the subject matter of this application also is related to the subject matter of U.S. patent application Ser. No. 60/269,260, priority to which is claimed under 35 U.S.C. § 119(e) and which is incorporated herein by reference. Further, the subject matter of this application is related to the subject matter of U.S. patent application Ser. No. 60/108,959, filed Nov. 18, 1998, and U.S. patent application Ser. No. 60/158,257, filed Oct. 6, 1999, all of which are incorporated herein by reference.

BACKGROUND OF THE INVENTION

1. Field of the Invention

The invention relates to devices and methods for treating incontinence. More specifically, particular embodiments of the invention use a variable control vacuum and/or vibratory device or other device to apply suction or other force to the male or female genital region, e.g. the region of the female urethral opening, the clitoral region and/or the vaginal region, or the male penile region.

2. Description of Related Art

A. Incontinence

Urinary incontinence is a significant clinical problem and a major source of disability and dependency. Although urinary incontinence is particularly prevalent in the elderly, it affects all age groups. Millions of male and female adult Americans suffer from urinary incontinence, including at least one-half of all nursing home residents. The monetary costs of managing urinary incontinence, and the psychological costs associated with the problem, are great. Fecal incontinence presents similar concerns.

The most frequently occurring types of urinary incontinence are stress incontinence, urge incontinence, overflow incontinence, and mixed incontinence. Stress incontinence is a common form of incontinence in women. Intra-abdominal pressure exceeds urethral pressure upon coughing, sneezing, laughing, lifting, or like activity, causing leakage of urine. Physical changes associated with pregnancy, childbirth, and menopause, for example, are known to cause stress incontinence.

Urge incontinence occurs when a patient loses urine while suddenly feeling the urge to urinate. The patient is unable to inhibit the flow of urine long enough to reach the toilet. Inappropriate bladder contractions are the most common cause of urge incontinence, and may occur in connection with central nervous system lesions, urinary infection, or bladder tumors, to name several examples.

Overflow incontinence occurs when the bladder is unable to empty normally. Weak bladder muscles, caused e.g. by nerve damage from diabetes, or a blocked urethra, caused e.g. by tumors or urinary stones, are among the more common causes of overflow incontinence. Frequency or urgency involves the need or urge to urinate on an excessively frequent or habitual basis. Combinations of these and other types of incontinence, e.g. stress incontinence and urge incontinence, are often called mixed incontinence.

Many options are available to treat incontinence in its various forms, including Kegel exercises, electrical stimulation, biofeedback, timed voiding or bladder training, medications, pessaries, implants, invasive or minimally invasive surgery, catheterization, and other methods and devices. Kegel exercises, or pelvic floor muscle exercises, for example, are intended to strengthen the muscles supporting the urethra, bladder, uterus and rectum. Weak pelvic floor muscles can contribute to urinary incontinence problems; hence strengthening those muscles can tend to alleviate those problems.

According to several known surgical treatment methods, one or more stimulation systems, including electrodes controlled by an electronic control system, are implanted to electrically stimulate nerves controlling external sphincter and bladder functions. The electronic control system directs the administration of electric pulses to stimulate the nerves appropriately. Note U.S. Pat. No. 4,771,779, for example, which is incorporated herein by reference. U.S. Pat. No. 6,055,456, also incorporated herein by reference, shows an implantable medical lead for stimulation of the sacral nerves to treat incontinence.

Although treatments requiring surgical intervention may be the preferred and most effective treatment mode in some situations, surgical intervention may be too extreme a measure in other situations. In some cases, surgical procedures to treat incontinence actually have a relatively low success rate; in many cases such procedures are irreversible. Additionally, a patient may hesitate to proceed with a surgical option, and/or a patient's physical condition may make surgical intervention inappropriate. Surgery may be inappropriate for pregnant patients, for example, or those of advanced age. Similarly, pharmacological treatment options may cause undesirable side effects and/or interactions with other medications. Non-surgical treatments, for example exercises or bladder training, may demand too high a degree of patient compliance or effort and thus may be resisted or otherwise ineffective.

A need exists, therefore, to treat urinary and/or fecal incontinence in a non-invasive, non-pharmacological manner that is less likely to meet with patient resistance or cause physical trauma or side effects.

B. Urogenital Anatomy

The female urethra passes just anterior to the vagina, and the external female urethral orifice is just posterior to the clitoris. The external urethral sphincter and the compressor urethrae compress the urethra and serve as functional sphincters. The pudendal nerve, which is derived from the anterior divisions of the ventral rami of S2 through S4, is the chief nerve of the perineum, providing sensation to the genitalia including the clitoris and controlling the motor function of the external urethral sphincter and the external anal sphincter. In the male, the pudendal nerve provides sensation from the penis and scrotum and provides motor control to the pelvic floor, including the anal sphincter.

C. Clitoral Anatomy

The clitoris in the human female consists of a cylindrical, erectile organ composed of three parts: the outermost glans or head, the middle corpus or body, and the innermost crura. The glans of the clitoris is visualized as it emerges from the labia minora, which bifurcates to form the upper prepuce anteriorly and the lower frenulum posteriorly. The body of the clitoris consists of two paired corpora cavernosa of about 2.5 cm in length. The body extends under the skin at the corona to the crura. The two crura of the clitoris, formed from the separation of the most proximal portions of the corpora in the perineum, attach bilaterally to the undersurface of the symphysis pubis at the ischiopubic rami.

A fibrous tunica albuginea ensheathes each corporal body made up of lacunar space sinusoids surrounded by trabecula of the vascular smooth muscle and collagen connective tissue. No retractor clitoridis muscle exists in humans as it does in other animals such as cattle and sheep, however a supporting suspensory ligament does hold the clitoris in the introital region.

The main arterial supply to the clitoris is from the ilio-hypogastric-pudendal arterial bed. The internal pudendal artery is the last anterior branch off the internal iliac artery. Distally, the internal pudendal artery traverses Alcock's canal, then terminates as it supplies the inferior rectal and perineal artery which supply the labia. The common clitoral artery continues to the clitoris. This artery bifurcates into a dorsal clitoral artery and a cavernosal clitoral artery.

In the normal female, autonomic efferent innervation of the clitoris passes from the pelvic and hypogastric nerves to the clitoris. Pelvic nerve stimulation results in clitoral smooth muscle relaxation and arterial smooth muscle dilation, causing an increase in clitoral cavernosal artery inflow and an increase in clitoral intracavernous pressure, which lead to tumescence and extrusion of the glans clitoris.

The clitoris has a dense collection of Pacinian corpuscles, Meissner's corpuscles, Merckel tactile disks, and free nerve endings. These sensory afferent nerves pass through the dorsal clitoral nerve to the pudendal nerve and into the sacral nerve roots (S2, S3, S4). (The male anatomy is completely homologous.) The presence of at least one somatic reflex arc is demonstrated by the bulbo-cavernosal reflex; squeezing the clitoris causes the anal sphincter to contract—the so-called "anal wink."

D. Female Sexual Dysfunction

Clitoral erectile insufficiency or reduced clitoral arterial flow may be caused by atherosclerosis, diabetes, or age-related causes, among other factors. Reduced clitoral arterial flow may lead to fibrosis of the clitoral cavernosa and reduced clitoral physiological function. In an animal model, Park et al. demonstrated that significant collagen synthesis occurs when the arterial inflow to the clitoris is compromised. This work demonstrated the importance of maintaining arterial flow to the clitoris to prevent collagen synthesis and fibrosis on the smooth muscle. See Park, K., et al., Vasculogenic Female Sexual Dysfunction: The Hemodynamic Basis for Vaginal Engorgement Insufficiency and Clitoral Erectile Insufficiency, IJIR, 9:27–37, 1997.

It is believed that the difficulty or inability to achieve clitoral tumescence may be related to and associated with other symptoms of female sexual arousal disorder. According to the International Consensus Report on Female Sexual Dysfunction, Female Sexual Arousal Disorder (FSAD) is defined as the persistent or recurrent inability to attain or maintain adequate genital lubrication or swelling responses resulting in personal distress. FSAD may be expressed as a lack of subjective excitement or lack of genital (lubrication/ swelling) or other somatic responses (AFUD Consensus Report of FSD, 1998).

A non-pharmacological approach to treatment that causes blood flow and engorgement, thereby applying a stimulus to the sensory nerve endings in the clitoris, periurethral area, and/or genital area, would be very beneficial to a large group of women complaining of FSAD.

SUMMARY OF THE INVENTION

Therapeutic devices and methods according to specific embodiments of the invention use a vacuum device and an applicator, e.g. a variable control vacuum device and a pliable cup, to apply suction to the genital region of a female patient. The suction and resultant clitoral and genital engorgement are believed to physically stimulate e.g. the sacral nerve roots 2–3–4. This physical stimulation is believed to improve neural control of e.g. the external and internal urethral sphincter muscles, including those in the bladder neck and mid-urethra, increase blood flow to the same muscles, generally prevent involuntary contraction of the urinary bladder, cause contraction of the muscles of the pelvic floor and correspondingly constrict the urethral sphincter and orifice, and/or produce advantageous effects by a different mechanism.

Simultaneously, certain embodiments of the invention encourage or cause clitoral engorgement and thus assist in the overall treatment of female sexual dysfunction over both short and long timeframes. According to one aspect, clitoral engorgement is believed to cause a reflex through the sacral nerves, resulting in vaginal arterial dilation and relaxation of the smooth muscles on the bladder, for example, thereby decreasing e.g. urge incontinence, urgency, and frequency.

A vacuum created over the clitoris, or suction applied to the clitoris, for example, creates a negative pressure in the clitoris that is or is likely to be lower than the systolic blood pressure. Alternatively, super-atmospheric pressure may be provided to produce massage or percussion of the clitoris and/or the surrounding area. In either case, the pressure differential tends to promote engorgement of the clitoris with blood and/or otherwise stimulate blood flow, providing the benefits described above while increasing the likelihood of short-term pleasurable effect and beneficial longer-term usage. Embodiments of the invention thus may encourage more regular and active compliance with a treatment program for urinary and/or fecal incontinence, while at the same time treating female sexual dysfunction if needed. Embodiments of the invention also are non-invasive, non-pharmacological, relatively inexpensive and easy to use.

Embodiments to address male urinary incontinence and male erectile dysfunction are also contemplated and disclosed, as are embodiments that use suction, vibration, massage percussion, and/or electrical stimulation, individually or in any partial or complete combination or sequence, or similar nerve or other stimulation to the penis, to achieve desired effects.

According to an aspect of the invention, an incontinence treatment device includes a suction applicator, the suction applicator being constructed for placement in association with the genital region of a patient to increase blood flow in the genital region, and a suction source in fluid communication with the suction applicator to create suction pressure in the suction applicator, wherein the suction applicator and suction source are constructed and arranged to cause physical stimulation of one or more nerves in the patient to alleviate incontinence in the patient. The suction applicator is constructed for placement in association with the genital region of a female patient to increase blood flow in the female genital region, according to one aspect, for example placement in association with the clitoris of the female patient to increase blood flow in the clitoris. The suction applicator can be constructed to completely cover the vaginal labia of a female patient, constructed to apply suction to the external urethral orifice of the female patient, and/or constructed for placement in association with the genital region of a male patient to increase blood flow in the male penis.

The incontinence treatment device also can include a device constructed and arranged to regulate the suction pressure drawn in the suction applicator and/or at least one sensor for sensing suction pressure in the suction applicator.

The suction applicator can include a pliable suction cup. The suction applicator also can include one or more electrical contact areas constructed to apply an electrical charge to the patient. The suction applicator and suction source can be constructed and arranged to cause physical stimulation of pudendal and/or sacral nerves and/or nerve roots in the patient, and can be free of structure constructed to receive and/or accommodate urine from the patient. A medication applicator can be connected to the suction applicator or the suction source, the medication applicator being constructed to apply a topical medication to the skin of the patient in the proximity of the suction applicator. The device can be constructed and arranged for treatment of urinary incontinence and/or fecal incontinence.

According to another aspect of the invention, an incontinence treatment device includes means, for placement in association with the genital region of a patient, for increasing blood flow and/or nerve activity in the genital region, and means for creating suction and/or vibratory pressure and/or electrical charge in the means for increasing, wherein the means for placement and the means for creating cause physical stimulation of one or more nerves in the patient to alleviate urinary and/or fecal incontinence in the patient. The device can include means for electrically powering the means for increasing and means for regulating the means for increasing, the means for regulating correlating suction force applied by the means for increasing to a desired level. The desired level can be blood-flow level, and/or related to urinary incontinence of the patient.

Another aspect of the invention provides a method of treating incontinence in a female patient, the method including applying a suction, pressure, and/or vibratory force to the clitoris, clitoral region, and/or external urethral orifice of the patient to encourage engorgement of the clitoris and/or periurethral tissues, and physically stimulating at least one nerve to alleviate incontinence in the patient. The method can further include applying a suction force to reduce intra-clitoral pressure and/or periurethral tissue pressure to a level below the systolic blood pressure of the patient. Incontinence is alleviated even after suction force is removed, according to an aspect of the invention. The method can further comprise electrically powering a suction device to apply the suction force, the applying of suction force e.g. occurring simultaneously with patient-directed tightening of pelvic muscles in the patient. The applying of suction force can occur in alternation with patient-directed tightening of pelvic muscles in the patient. The physical stimulation of the at least one nerve alleviates urinary and/or fecal incontinence in the patient.

According to another aspect of the invention, an incontinence treatment device includes a housing, a vacuum cup in fluid communication with the housing, the vacuum cup having an opening constructed for placement over the clitoris of a female patient, an airflow device in fluid communication with the vacuum cup, the airflow device increasing suction pressure in the vacuum cup to draw blood into the female clitoris, and a modulator, operably coupled with the vacuum cup, to vary the suction pressure in the vacuum cup and promote recycling of arterial blood in the clitoris, wherein the housing, vacuum cup, airflow device and modulator are constructed and arranged to alleviate incontinence in the patient. The airflow device can include a motor. The vacuum cup opening can be a first opening, and the modulator can include a second opening operably coupled with the vacuum cup. The second opening is disposed in a wall of the housing.

According to another aspect of the invention, a method of treating incontinence in a female patient includes providing a suction applicator constructed for placement over the genital region of a female patient, placing the suction applicator in fluid communication with a suction source to create suction pressure in the suction applicator, placing the suction applicator in association with the clitoral region of a female patient, activating the suction source to create said suction pressure and increase blood flow and sacral nerve activity in the genital region, and alleviating incontinence in the patient.

According to another aspect of the invention, an incontinence treatment device includes an applicator constructed for contact with the body of a patient in the area of at least one nerve of the patient, and an activation device, operably coupled with the applicator, for activating the applicator to stimulate at least one nerve of the patient to alleviate incontinence of the patient. The incontinence treatment device can include an airflow device for causing airflow in the applicator. The airflow device can be constructed to cause a suction force in the applicator for applying suction to the body of the patient to alleviate incontinence of the patient, and/or constructed to cause super-atmospheric pressure in the applicator for applying pressure to the body of the patient to alleviate incontinence of the patient. The applicator can include an electrical contact for applying an electrical charge to the body of the patient to alleviate incontinence of the patient. The incontinence treatment device can include an off-cup electrical contact for applying an electrical charge to the body of the patient to alleviate incontinence of the patient. The applicator can be constructed for contact with the clitoris or clitoral region of a female patient to promote clitoral engorgement, constructed for contact with the penis or penile region of a male patient, and/or constructed for contact with one or more of the anus, vagina, and labia.

Other features and advantages of the invention will be apparent from the remainder of this application.

BRIEF DESCRIPTION OF THE DRAWINGS

Embodiments of the invention will be described with respect to the figures, in which like reference numerals denote like elements and in which:

FIG. 4 is a top view of an incontinence treatment device according to an embodiment of the invention;

FIG. 5 is a side view of the FIG. 4 device;

FIG. 6 is a bottom view of the FIG. 4 device;

FIG. 7 is a rear view of the FIG. 4 device;

FIG. 8 is a front view of the FIG. 4 device;

FIG. 31 is a table reflecting clinical data;

FIG. 32 is an additional table reflecting clinical data;

DETAILED DESCRIPTION OF PREFERRED EMBODIMENTS

Figure 1:
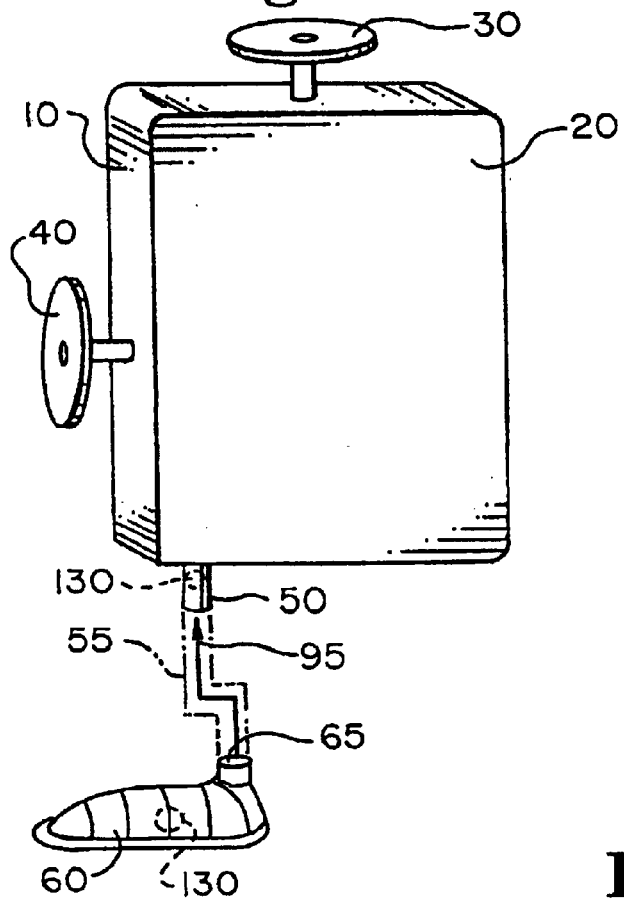
FIG. 1 is a perspective, schematic view of an incontinence treatment device according to an embodiment of the invention.

Devices according to aspects of the invention physically stimulate sacral nerves and nerve roots and/or other nerves or areas to reduce or eliminate urinary incontinence, e.g. stress, urge, and/or overflow incontinence, and/or fecal incontinence. Embodiments of the invention also tend to promote blood flow to the genital region, e.g. to the clitoris of a female patient or the penis of a male patient, to also treat female sexual dysfunction or male erectile dysfunction if needed. Non-pharmacological, non-invasive treatment of incontinence, especially (although not limited to) urge incontinence, is achieved in a previously unknown and advantageous manner.

Embodiments of the invention are expected to become a primary therapy for treating overactive bladder symptoms or similar incontinence symptoms, because of the many advantages provided over current treatments. Kegel muscle exercises, although often perceived useful for treating incontinence symptoms, can be difficult to implement in practice, in part because many patients have difficulty knowing which muscle to contract. Biofeedback or other treatments using vaginal probes or the like are often perceived as uncomfortable or invasive. Treatment using e.g. an electromagnetic chair or other large or complex appliance requires an office visit and involves corresponding inconvenience and expense. Other treatments are surgically invasive and thus even more expensive, inconvenient and prone to negative side effects. Pharmacological treatments, of course, also can produce negative side effects. Embodiments of the invention, on the other hand, are non-invasive, non-pharmacological, easy-to-use in the privacy of the patient's home, free of serious risk factors, and provide other advantages.

As referenced above, it is generally accepted that mild electrical stimulation of the sacral nerves in the nerve root or at the peripheral sciatic nerve can be used in the treatment of urinary incontinence. The sacral nerves influence the behavior of e.g. the external urethral orifice, the bladder, and the muscles of the pelvic floor. It is also generally accepted that clitoral stimulation and tumescence are important aspects of female sexual arousal. Tumescence or engorgement occurs when the clitoris fills with blood. During sexual arousal, the smooth muscles within the clitoris relax and the arterial wall dilates. This causes an increase in blood flow leading to tumescence and extension of the glans clitoris. Although a physical relationship exists between proper urinary function and sexual stimulation (e.g. urination is difficult or impossible during periods of sexual stimulation), it has not been generally known in theory or practice to treat urinary and/or fecal incontinence by physically stimulating sacral nerves and/or sacral nerve roots by using a device that also can successfully treat female sexual arousal disorder, or male erectile dysfunction, by applying suction or pressure to or otherwise stimulating e.g. the female genitalia or genital region, or by applying suction or pressure to or otherwise stimulating the male penis by using e.g. a vacuum cylinder.

Certain physical conditions which cause constriction of the vaginal and clitoral arteries may interfere with or prevent a woman from achieving clitoral tumescence. It is believed that the difficulty or inability to achieve clitoral tumescence may be related to other symptoms of female sexual dysfunction, such as lack of desire, difficulty achieving orgasm, insufficient vaginal lubrication, and painful intercourse. See Goldstein, I. and Berman, J., Vasculogenic Female Sexual Dysfunction: Vaginal Engorgement and Clitoral Erectile Insufficiency Syndrome. *International Journal of Impotence Research,* 10 Supplement 2, S84–S90, 1998, which is incorporated herein by reference. Such symptoms and difficulties also may share a link with causes of certain types of urinary urge, overflow and/or stress incontinence, and/or fecal incontinence.

Embodiments of the invention are designed to cause certain nerve responses or otherwise minimize urinary and/or fecal incontinence in one or more of the various forms, increase blood flow in the clitoris to assist a woman to achieve clitoral engorgement, and otherwise be applicable to the treatment of incontinence and/or the treatment and diagnosis of female sexual disorders. Embodiments of the invention increase blood flow by creating a vacuum around and/or using increasing pressure to produce percussion and/or massage of e.g. the clitoris, the labia, the external urethral orifice and/or other areas of the female genital region. Pelvic nerve stimulation, such as that caused by suction to and/or engorgement of the clitoris, or suction to the vagina, vaginal wall and/or external urethral orifice, for example, results in clitoral smooth muscle relaxation and arterial smooth muscle dilation via an autonomic spinal reflex arc. This relaxation and dilation result in an increase in clitoral cavernosal artery inflow and an increase in clitoral intracavernous pressure, which lead to tumescence and extrusion of the glans clitoris, according to specific embodiments of the invention.

More specifically, embodiments of the invention are believed to create pudendal nerve input into the pelvic floor and external sphincter. As the external sphincter contracts, an impulse is believed sent through the afferent limb of the pelvic nerve, up to the spinal cord at S2, S3 and S4, inhibiting pelvic nerve activity that can contribute to e.g. urinary incontinence. In other words, pelvic nerve activity is inhibited by enhancing pudendal nerve activity according to embodiments of the invention. The pudendal nerve is the primary neurological pathway for the clitoris, both afferent and efferent. With respect to the external sphincter, the efferent aspect is the pudendal nerve, and the afferent aspect is the pelvic nerve. Impulses are sent to the spinal cord, according to embodiments of the invention, where they affect the limb of the pelvic nerve that innervates the bladder. Embodiments of the invention are expected to provide a durable response, meaning that the reduction or elimination of incontinence symptoms will continue even after treatment ceases.

Embodiments of the invention can be used in combination with Kegel exercises to stimulate the sacral nerves, sacral nerve roots and/or other areas while simultaneously strengthening the muscles of the pelvic floor. The involuntary Kegel-type muscle action that occurs during orgasm produced during use of the invention in its various embodiments also can have a beneficial effect. Use in combination with other therapies or treatments is also contemplated according to embodiments of the invention.

One particular device according to an embodiment of the invention includes a battery-operated or manual vacuum pump and a disposable vacuum cup, for example. The vacuum cup is placed over and is sized to include the clitoris and/or other parts or all of the perineum, and the pump is activated to create a vacuum. The vacuum draws blood into the clitoris, causing tumescence, and/or into other areas in the female genital or abdominal region. Such placement and activation by physically stimulating e.g. sacral nerve roots are beneficial in the treatment of urinary and/or fecal incontinence in the various forms.

According to aspects of the invention, the vacuum cup is attached to the vacuum pump and is activated by a button or switch on the vacuum pump or a housing thereof. A control valve, e.g. on an opposite side of the vacuum pump or housing, controls the amount of vacuum applied. The vacuum cup is supplied sterile or non-sterile, according to embodiments of the invention, and can be cleaned e.g. with soap and water.

According to one embodiment, the device is a prescription-only device intended for use by only one patient. Embodiments of the invention have the potential to be used both as non-pharmacological treatment alternatives to urinary and/or fecal incontinence in the various forms, and/or female sexual arousal disorder, and/or as long-term therapy to recondition clitoral smooth muscle and restore normal blood flow and clitoral engorgement. Further aspects of the invention will be apparent from the remainder of this description.

Figure 2:
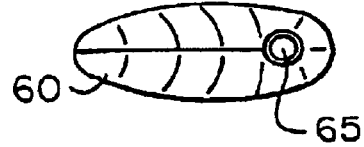
FIG. 2 is a top view of a vacuum application mechanism for use with the embodiment of FIG. 1.
Figure 3:
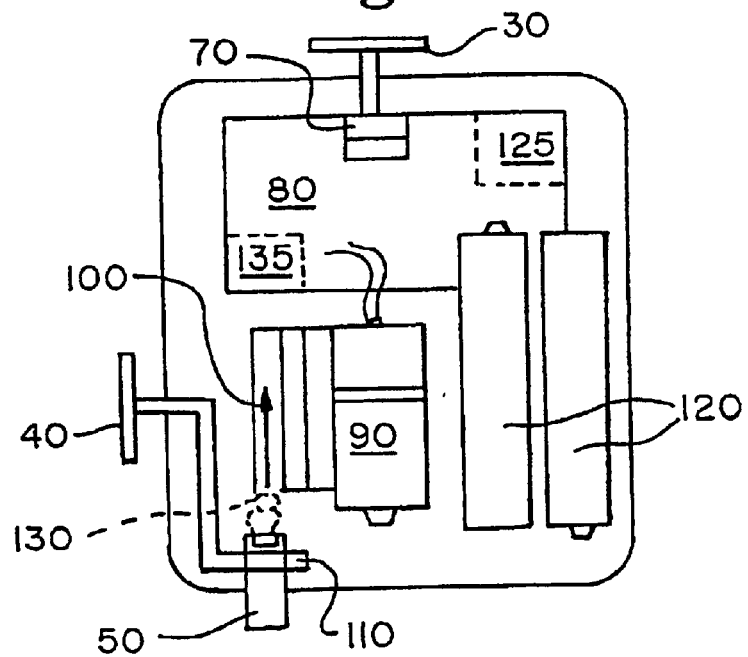
FIG. 3 is a schematic view of the incontinence treatment device of FIG. 1.

One embodiment of an incontinence treatment device according to the invention is shown in FIGS. 1–3. Device 10 includes housing 20, which accommodates on/off switch 30, optional vacuum release 40, and vacuum connection device 50, to which a length of e.g. flexible tubing 55 or other fluid-conveying apparatus can be readily releasably connected. The end of tubing 50 remote from housing 20 supports vacuum or suction applicator 60. According to one embodiment, applicator 60 is a disposable vacuum or suction cup that is specially configured for application to the clitoris and/or the clitoral region. Alternative embodiments are of different sizes and/or shapes, or the same shape, for application to the external urethral orifice, labia, anus, vagina and/or other areas of e.g. the female genital region and/or perineum, alone or in combination. Thus, according to one embodiment, vacuum cup 60 is configured for application only to the external urethral orifice. According to another embodiment, vacuum cup 60 is configured to cover the entire genital region, from the clitoris to the opposite end of the vaginal opening, or toward or all the way to the anal opening. Although application to the clitoris or clitoral region is believed to provide the most innervated pathway, other placements in connection with other anatomical structures are also contemplated.

Vacuum cup 60 can be readily removably attached to tubing 55 at aperture 65, and/or tubing 55 is readily removably attached to connection device 50, to facilitate interchangeability of components e.g. between patients or uses. According to preferred embodiments, applicator 60 is of elliptical shape, as shown, and can be soft and pliable. FIG. 2 is a top view of applicator 60.

FIG. 3 shows internal components of device 10, according to one embodiment. On/off switch 30 is mechanically, electrically, or otherwise connected to a corresponding on/off activation portion 70 of optional control electronics 80 for device 10. Electronics 80 comprise one or more signal-handling devices for handling electrical signals, e.g. data signals. Electronics 80 are operably coupled with vacuum pump/motor device 90, which is constructed to draw a vacuum or suction as indicated by arrows 95 (FIG. 1) and 100 (FIG. 3). One type of pump/motor device 90 possible for use is a small diaphragm pump available from Virtual Industries, Inc., Colorado Springs, Colo. Vacuum release 40 is operably coupled to vacuum connection device 50 and/or a portion of the housing for pump/motor 90, to effect vacuum release through vent 110, as desired.

Device 10 is electrically operated according to embodiments of the invention, e.g. by two 1.5 volt batteries 120. However, A/C operation or operation by other battery configurations is also contemplated. Further, a manual or oral suction or vacuum-generating device, or a manual pump, for example a squeeze ball with a one-way valve, may be used in place of pump/motor device 90, as can a hydraulic suction device using e.g. water or other fluid via the Venturi effect.

Electronics 80 can include one or more processing devices 125, e.g. a microprocessor, operably connected to one or more sensing devices 130 that sense vacuum or suction pressure applied to the clitoris or clitoral region. Sensor(s) 130 can be located e.g. at pump/motor 90, vacuum cup 130, vacuum connection device 50, or some other location. Data regarding the vacuum level or pressure level can be continuously or intermittently generated, monitored, and/or recorded in memory 135 of electronics 80, for later or substantially simultaneous display, downloading, and/or analysis. Further, electronics 80 can include vacuum regulation protocols that automatically correlate the amount of vacuum or suction drawn by pump/motor 90 or other device to the degree of sexual arousal (as monitored by e.g. pelvic, vaginal, clitoral, labial and/or other blood-flow measurement devices using e.g. ultrasound or impedance plethysmography, or other suitable apparatus, such as the devices and principles discussed in e.g. U.S. Pat. Nos. 6,169,914, 6,251,076, and 6,015,393, all assigned to UroMetrics, Inc., St. Paul, Minn., and all of which are incorporated herein by reference), degree of nerve stimulation, urodynamic measurements such as pressure profiling, or other degree of body response or indicator. Such correlations can be selected according to the physiological characteristics of a particular patient, for example. Further, vacuum/suction data, arousal data, and/or other data can be compared to a control or to data from other patients. Device 10 can be used in the diagnosis of blood-flow insufficiency, which is often a cause of female sexual arousal disorder.

Alternatively, electronics 80 can be substantially eliminated or reduced with on/off switch 30 substantially alone being used to activate pump/motor 90. In that case, switch 30, substantially alone, is a signal-handling device that handles electrical signals that are ultimately related to the suction pressure created. Switch 30 can also be configured such that release of switch 30 releases suction pressure automatically.

In use, applicator 60 is placed over the female clitoris or clitoral region, or over one or more of the other organs or regions referenced above. On/off switch 30 is activated to initiate a vacuum or suction in applicator 60 via pump/motor device 90 or other source. When a desired amount of data has been read and/or stimulation or treatment achieved, on/off switch 30 can be activated again and vacuum release 40 depressed to allow the applied vacuum to be released to atmospheric or ambient pressure. With other embodiments, release or subsequent activation of on/off switch 30 serves to release the applied vacuum.

FIGS. 4–8 illustrate an additional specific embodiment of the invention. Incontinence treatment device 200 includes a generally curved outer casing 210 for comfortable and convenient gripping by a human hand. Casing 210 is injected molded using standard techniques, according to one embodiment, and can be formed of ABS Class 6 medical-grade plastic, for example. According to one embodiment, casing 210 is formed of Dow Chemical Company's ABS Resin called MAGNUM 9555. A biocompatible material is highly preferred, to ensure that it will not cause adverse tissue reactions when placed in contact with the patient's skin.

According to one embodiment, casing 210 is about 4.2 inches long and about 2.4 inches wide at its widest point. Of course, other dimensions are contemplated as well.

Externally, casing 210 can be water resistant or waterproof, electrically insulated, formed with areas suitable to accommodate a company or device name or logo (e.g. by using stick-on labels or removable mold insets), and/or of an esthetically pleasing color (e.g. pastel) and texture (e.g. light roughness). Indents 215 are provided for esthetic reasons and may provide a thumbhold to allow better gripping of casing 210. Casing 210 also is sized sufficiently to accommodate a variety of internal components, to be described.

Extending from casing 210 is suction applicator 220. According to the illustrated embodiment, applicator 220 includes neck 230 ending in vacuum cup 240. According to alternative embodiments, applicator 220 can include only cup 240 with a substantially shortened or non-existent neck 230. Applicator 220 is about 2 inches long, according to one embodiment. Further, applicator 220 can be extended by tubing, for example ⅛ in. inner diameter by ¼ in. outer diameter tubing. Such tubing can be about 12 in. long, for example, and be either one-piece with applicator 220 or removably or non-removably connected to it. According to alternate embodiments, suction applicator 220 can operate as a pneumatic or hydraulic applicator.

Vacuum cup 240 can be formed of two portions: rigid portion 243 for permanent or removable connection to neck 230, if any, and soft, skin-contacting portion 245. Rigid portion 243 advantageously is formed of a biocompatible polyethylene or polypropylene, according to one embodiment. Soft, skin-contacting portion 245 also can be formed of a biocompatible material, e.g. a silicone material or the thermoplastic elastomer C-FLEX available from Consolidated Polymer Technology. Skin-contacting portion 245 has a durometer of 4A, according to one embodiment, and should be pliable enough and/or shaped so as to form a vacuum-tight seal.

According to additional embodiments, rigid portion 243 can be constructed of elastic material or otherwise can be constructed to store energy from subatmospheric or superatmospheric pressure pulses, for example. Further, skin-contacting portion 245 can also include an adhesive material to promote better maintenance of contact with the patient's skin.

Applicator 220 can be generally translucent or transparent, at least for those portions that do not contact the patient's skin. It also can be desirable that applicator 220, or at least vacuum cup 240, be constructed of a disposable material. Disposal between uses and/or between patients is to be encouraged, e.g. to prevent cross-contamination and promote cleanliness. Additional features of applicator 220 will be described below.

Casing 210 also includes battery door 260, which allows access to a battery compartment to be described. Of course, alternative power sources are contemplated, e.g. A/C or D/C power sources operably coupled to casing 210 and its internal components by appropriate mechanisms, e.g. wiring. Mechanical, hydraulic, manual, oral, and other power sources and/or suction sources are also contemplated.

Extending from casing 210 is on/off switch 270. Switch 270 can be a low-noise, soft-touch device positioned for easy access by the finger or hand of the patient or the patient's partner. Switch 270 can take any of a number of known forms, e.g. a slider switch, wheel, push-button, etc.

Also extending from casing 210 is air bleed valve control 280, for example in the form of a wheel. Air bleed wheel 210 allows adjustment of vacuum pressure, for example in the 0–10 in. Hg (inches of mercury) range, in a manner to be described. Wheel 280 can have a grooved texture for easy turning. Alternatives to a wheel-type activator also are contemplated, for example a slider switch or other mechanism. Wheel 280 also can be used to adjust pneumatic or hydraulic pressure, according to particular embodiments.

Vacuum modulator 290 also optionally extends from the side of casing 210 and includes an aperture fluidly connected to the interior of casing 210. By manually covering and uncovering the aperture and/or other means of electrical or mechanical control with e.g. a finger of the patient or of the patient's partner, suction pressure in the suction applicator can be varied, rapidly if desired, to promote stimulation of the clitoral region, the pudendal nerve, and the sacral nerve and nerve roots (S2, S3, S4), or otherwise provide a desired effect with respect to e.g. the treatment of urinary and/or fecal incontinence in the various forms. Additionally, modulation of suction pressure serves to refresh arterial blood flow in the clitoris or other area. By cycling arterial blood, the blood is better able to pick up collagen from e.g. the clitoral vasculature and accelerate its removal. Removal of collagen build up and reversal of fibrosis on the smooth muscle thus is facilitated and encouraged. Other vacuum modulation embodiments are described below.

Figure 9:
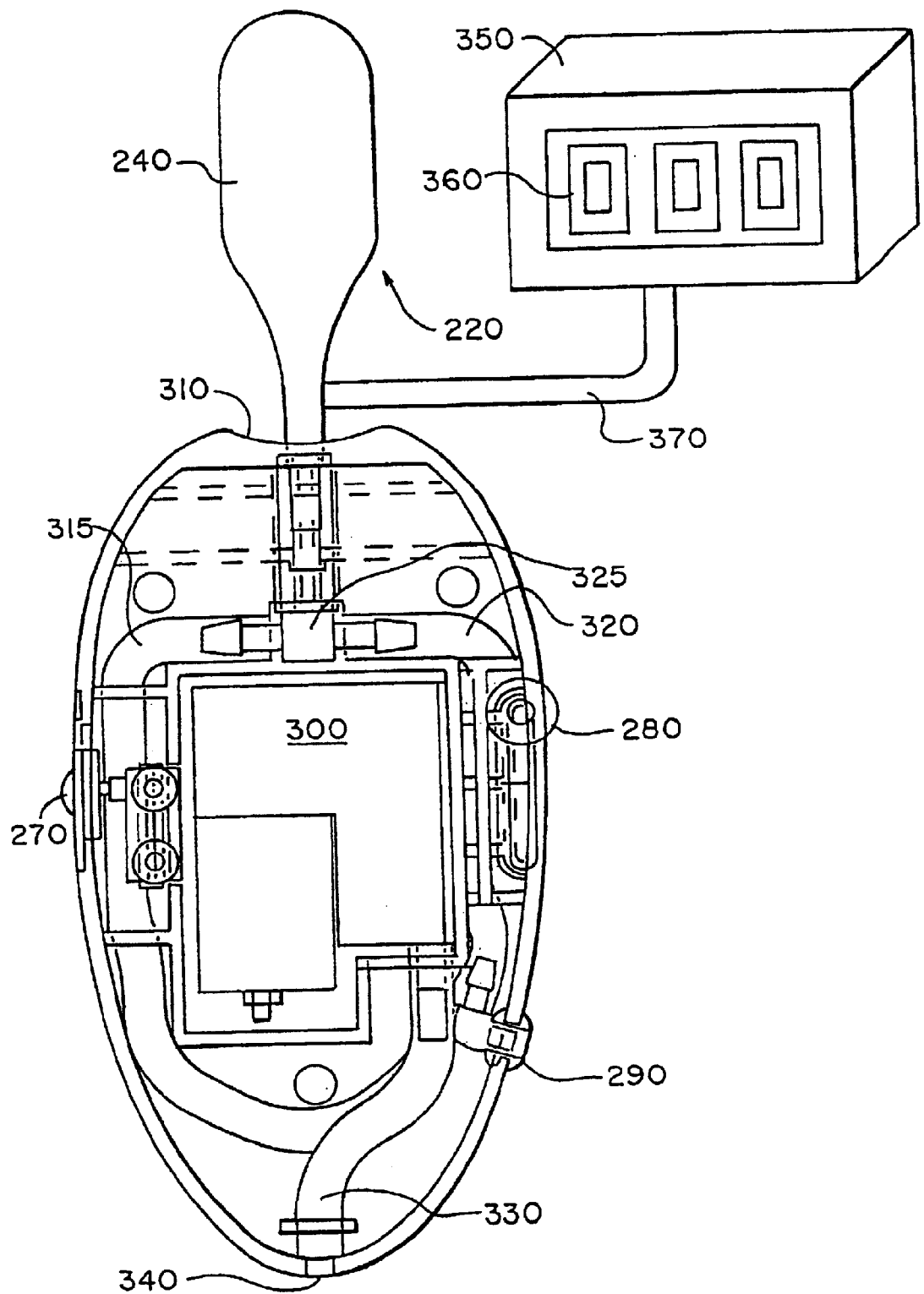
FIG. 9 is a top cross-sectional view of the FIG. 4 device, with an optional pressure gauge illustrated schematically.
Figure 10:
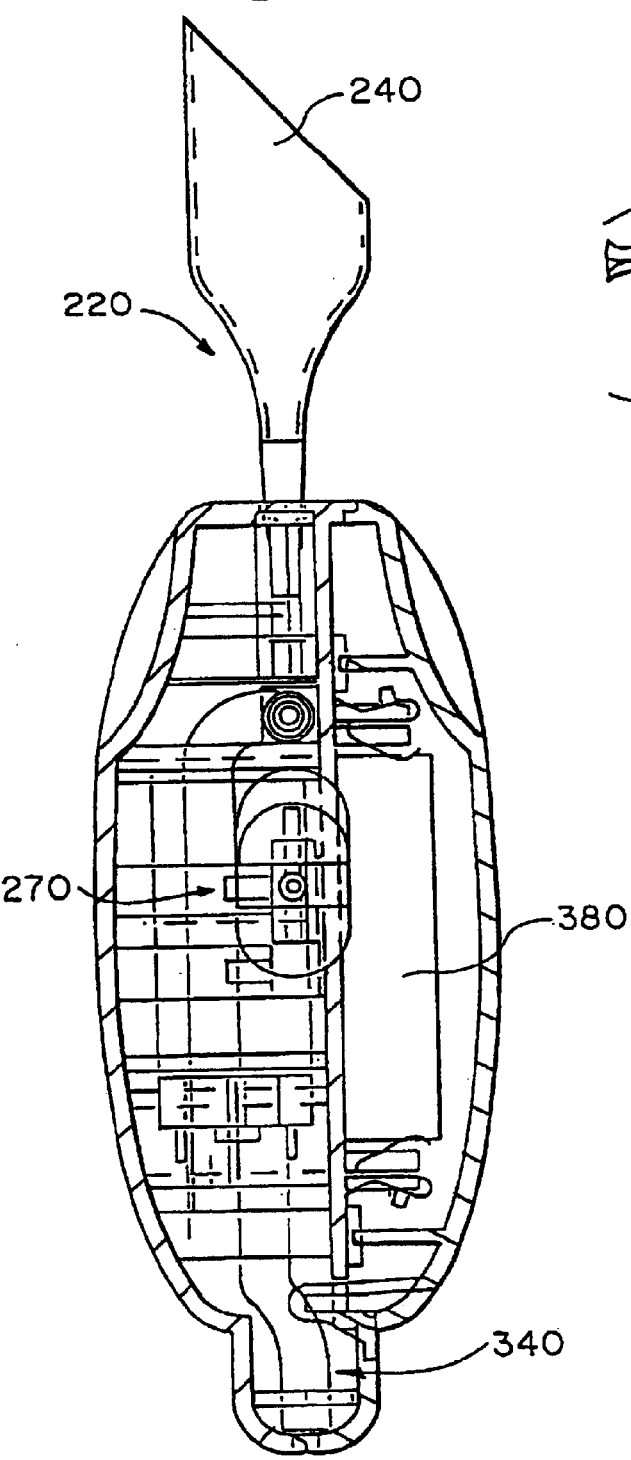
FIG. 10 is a side cross-sectional view of the FIG. 4 device.

FIGS. 9–10 show interior components within casing 210. This embodiment of the invention swaps the locations of air bleed wheel 280 and vacuum modulator 290 relative to the embodiment of FIGS. 4–8, and also adjusts the location of on/off switch 270. Of course, these switches and controls can be placed at any desired portion along casing 210.

Vacuum pump/motor assembly 300 generates a vacuum within applicator 220, drawing air through vacuum intake 310 to which applicator 220 is operably fluidly connected. Pump/motor assembly 300 is connected to intake 310 via draw tube 315, for example. Vacuum leak tube 320 extends from vacuum T-junction 325 in a direction generally opposite to draw tube 315, according to the illustrated embodiment, and is operably fluidly connected to air bleed wheel 280. Exhaust tube 330 connects pump/motor assembly 300 with exhaust port 340.

Vacuum pump/motor assembly 300 pulls a vacuum of 0–10 in. Hg (inches of mercury), for example, and is constructed and arranged for smooth and quiet operation. Pump/motor assembly 300 operates at a speed compatible with air bleed system 280. An OEM Micro Air Pump available from Virtual Industries, Inc., Colorado Springs, Colo., is an example of a pump/motor useable according to the invention, with dimensions of about 1.83 in×0.68 in×1.22 in, a weight of about 1.2 ounces and a maximum suction of about 13 in. Hg. When installed within device 200, pump/motor assembly 300 pulls a maximum of about 9.8 in. Hg, according to one embodiment. According to other embodiments, pump/motor assembly 300 provides pneumatic and/or hydraulic actuation to create e.g. vibration, percussion, subatmospheric pressure and/or super-atmospheric pressure, or modulation of these effects.

FIG. 9 also illustrates gauge 350 with digital display 360, operably coupled with applicator 220. According to one embodiment, gauge 350 is a vacuum pressure gauge displaying vacuum pressure in inches of mercury. Tube 370 is directly fluidly connected to gauge 350 and to applicator 220. A pressure transducer or other sensing element can be positioned in a desired location relative to applicator 220, tube 370 or within gauge 350 itself, as with previous embodiments.

Figure 11:
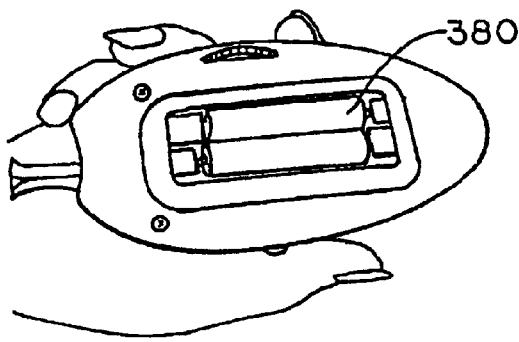
FIG. 11 is a view of the FIG. 4 device with a battery cover portion removed.

One or more batteries 380, shown in FIGS. 10 and 11, power pump/motor assembly 300 and are positioned behind battery door 260. According to one embodiment, device 200 can run for about 3–5 hours on 2 1.5 volt AAA batteries, for example of the alkaline type. Terminals and springs provided to contact batteries 380 can be corrosion resistant. Proper battery insertion is clearly marked, sufficient electrical contact is generally easy to achieve, and the batteries generally are easy to remove.

Figure 12:
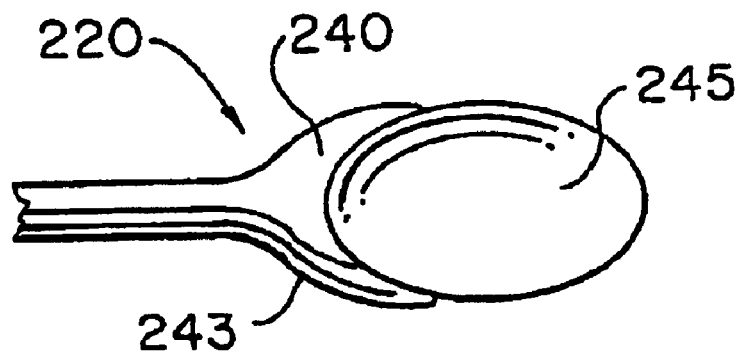
FIG. 12 is a bottom view of a vacuum cup of the FIG. 4 device.
Figure 13:
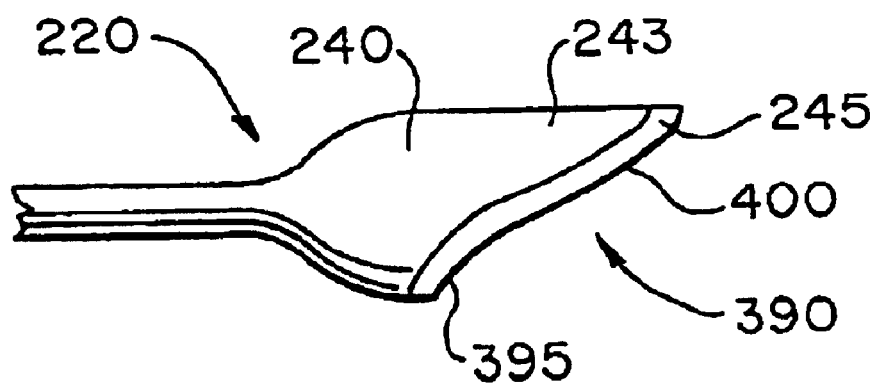
FIG. 13 is a side view of the FIG. 11 vacuum cup.

FIGS. 12–13 illustrate vacuum cup 240 of applicator 220, with rigid portion 243 and soft portion 245 as described previously. Cup 240 includes contact surface 390, which is specifically constructed and arranged for application to the clitoral region of the patient. Contact surface 390 includes concave portion 395, as shown at the lower edge of contact surface 390 in the side view of FIG. 13, and convex portion 400, as shown at the upper edge of contact surface 390. The combination of contact surface 390, soft portion 245 and underlying/supporting rigid portion 243 provides advantageous modes of contacting the clitoral or other region of a female patient.

Applicator 220 and/or vacuum cup 240 are specifically sized to suit the typical female clitoris or other desired organ or region. Although actual sizing can vary and can depend directly on the anatomy of the intended patient, one specific embodiment of vacuum cup 240 includes an outer diameter of about 0.90 in. and an inner diameter of about 0.75 in. Neck 230, on the other hand, includes an outer diameter of about 0.15 in. and an inner diameter of about 0.06 in., according to this embodiment.

Figure 14:
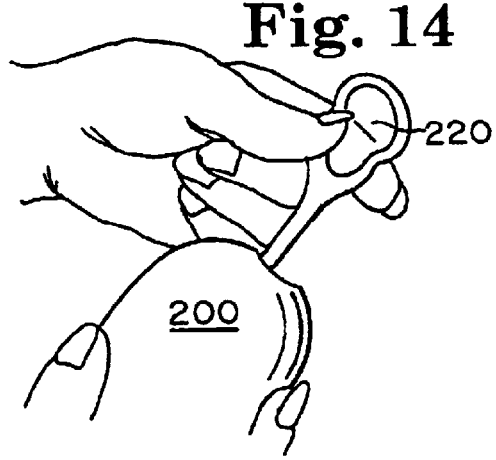
FIG. 14 is a top perspective view of the FIG. 4 device.

FIG. 14 illustrates insertion/removal of applicator 220 to/from device 200, e.g. for cleaning or disposal. Applicator 220 can be cleaned with e.g. soap and water, as can casing 210 of device 200. Applicator 220 should be completely dry before it is reconnected to device 200.

In use, applicator 220 is attached to vacuum intake 310 in casing 210, as shown in e.g. FIG. 14. The patient or partner activates device 200 by activating on/off switch 270, turning pump/motor assembly 300 on and thereby drawing air into and through applicator 220. At this point it is recommended that the patient turn air bleed wheel 280 so that the vacuum is at its lowest setting. According to one embodiment, rotation of wheel 280 toward applicator 220 decreases vacuum pressure, and rotation away from applicator 220 increases vacuum pressure.

Figure 15:
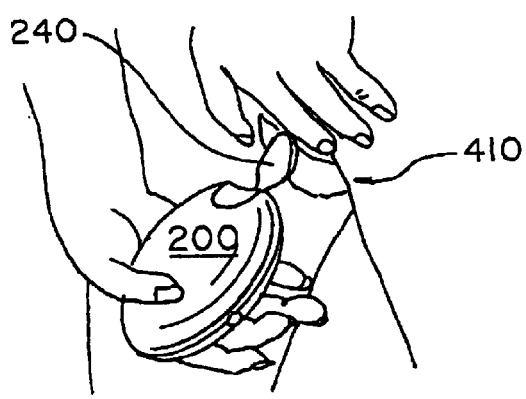
FIG. 15 shows the FIG. 14 device in use.

The labia majora (outer skin) should be gently opened, exposing the clitoris, according to one embodiment, and then vacuum cup 240 placed over the clitoris or other desired area. Applying a slight pressure will gently compress soft portion 245 between rigid portion 243 and clitoral region 410, as shown in FIG. 15, obtaining a seal around the clitoris or other region. Air bleed wheel 280 then is rotated to obtain the desired level of vacuum.

Figure 16:
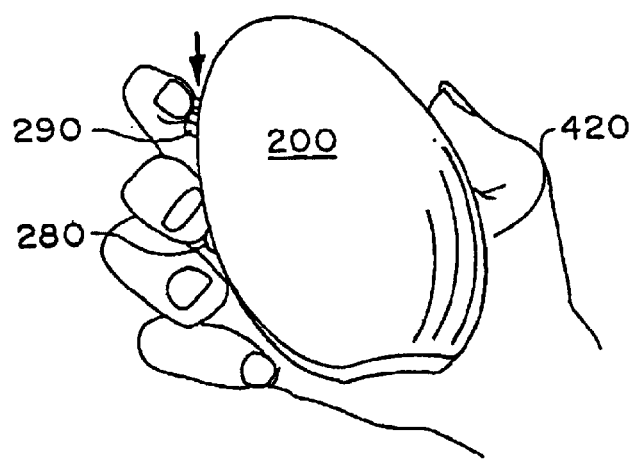
FIG. 16 shows use of a vacuum modulator or a massage or percussion modulator according to an embodiment of the invention.

Vacuum modulator 290 then can be used to pulsate the vacuum level, as depicted in FIG. 16. The patient, or her partner, places a finger over the aperture in modulator 290 to increase vacuum level and removes the finger to decrease it. Modulator 290 has the best effect when air bleed wheel 280 is set to less than maximum vacuum. FIG. 16 also illustrates that device 200 is easily grasped in hand 420.

When applied to the clitoris, the vacuum applied by device 200 will cause the clitoris to become engorged, i.e. filled with blood. Vacuum level and modulation can be adjusted by either the patient or her partner, as needed, to maintain engorgement. Thus, embodiments of the invention provide the ability both to rapidly modulate vacuum pressure with modulator 290, in a manner akin to the modulation of alternating current, for example, and simultaneously to more evenly hold underlying vacuum pressure at a substantially constant level or gradually change it, e.g. with wheel 280, in a manner akin to direct current. This dual functionality provides substantial advantages over the prior art.

Vacuum modulation of the type described above, or simple switching-on and switching-off of suction e.g. by electronics or repetitive removal/application of vacuum cup 240, can be used in combination with placement of cup 240 over e.g. the external urethral orifice and use of Kegel-exercise therapy in the treatment of incontinence in its various forms. According to one example, stronger vacuum can be applied simultaneously with or in alternation with the tightening of the pelvic floor muscles that occurs during the Kegel exercise. Treatment of male incontinence in this manner, according to corresponding embodiments of the invention described herein, is also contemplated.

Figure 17:
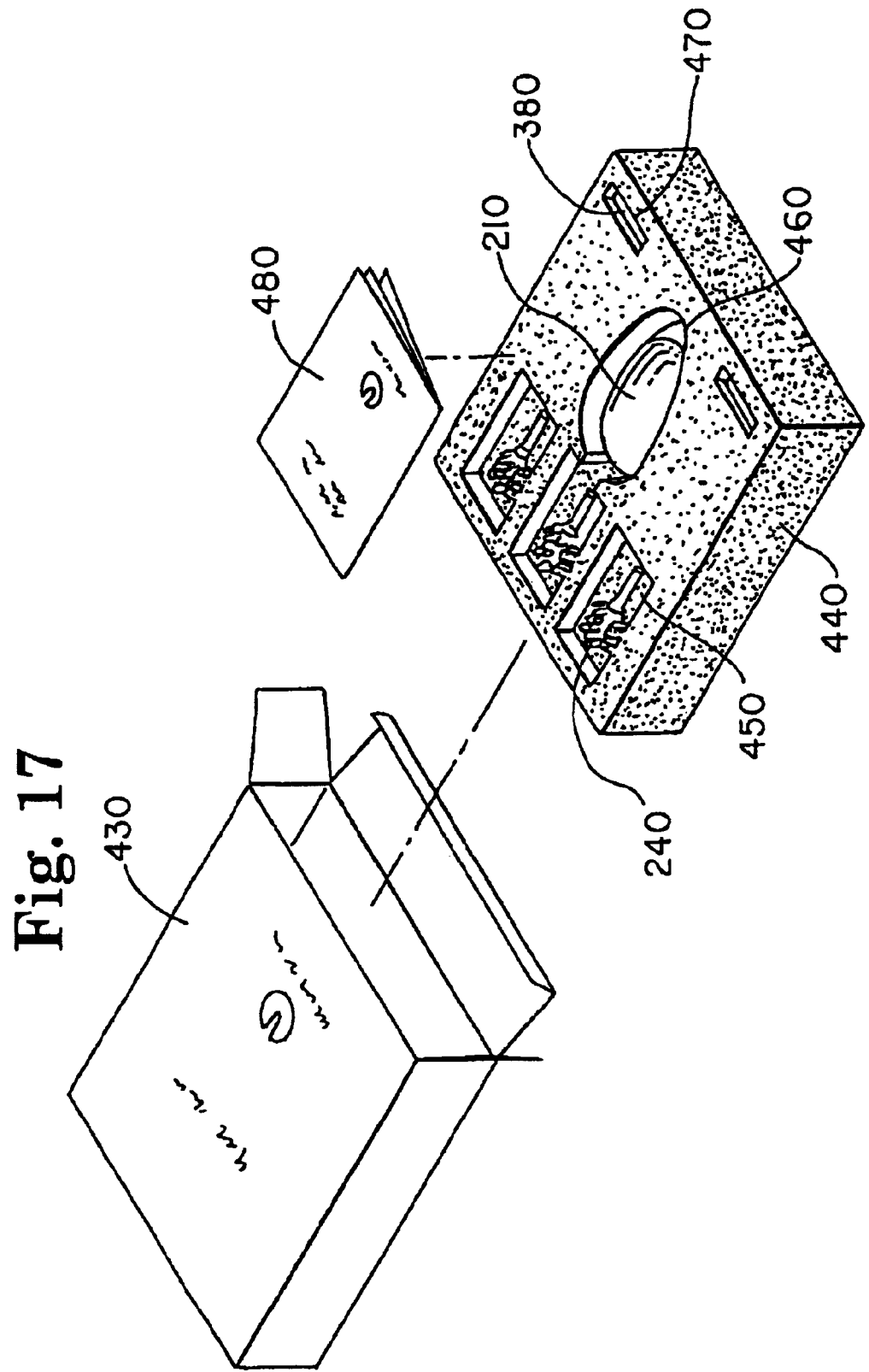
FIG. 17 shows packaging materials according to an embodiment of the invention.

FIG. 17 illustrates one packaging embodiment according to the invention. Box 430, made of cardboard or other suitable material, is of approximate dimension 7.5×7.5×2.5 inches. Of course, other dimensions to are contemplated as well. Insert 440 fits within box 430 and is made of e.g. 2 lb. density polyurethane, foam rubber or another shock-absorbing and cushioning material that generally holds its shape when uncompressed. Insert 440 defines one or more indents 450 for accommodating vacuum cups 450, indent 460 for accommodating casing 210, and one or more indents 470 for accommodating batteries 380. Patient instruction manual and/or other literature 480 can be disposed over insert 440. Of course, other forms of packaging are contemplated according to the invention.

Figure 18:
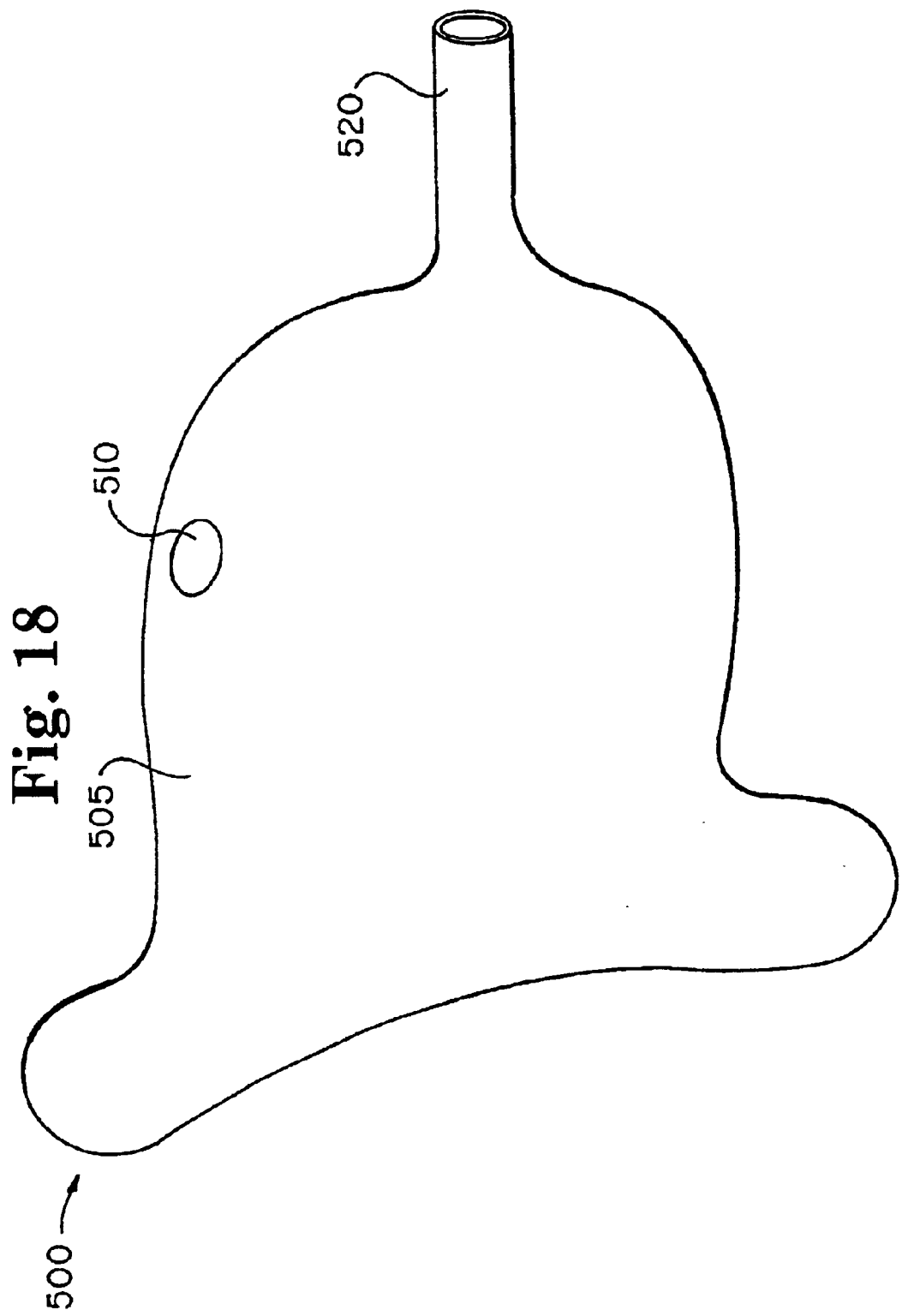
FIG. 18 shows a vacuum cup according to an embodiment of the invention.

FIG. 18 illustrates an alternative applicator embodiment. Applicator 500 of this embodiment includes vacuum cup 505 with one or more modulation ports 510 and optional neck 520. The illustrated modulation port 510 extends through a wall of vacuum cup 505 for manual covering and uncovering with a finger, as with previous embodiments. Varying the suction pressure in cup 505 in this manner tends to promote engorgement of the clitoris, and stimulation of the pudendal nerve, sacral nerve and nerve roots (S2, S3, S4), as previously described, and facilitates the removal of collagen buildup and reversal of fibrosis.

Disposing the modulation port through a wall of the vacuum cup instead of at the side of the handheld housing presents several advantages. Finger-actuated modulation of vacuum is achieved simply and effectively, and manufacturing complexity and cost are reduced. Additionally, when the patient's finger or the partner's finger is placed over the modulation hole, the hand/fingers are automatically well-placed to assist in manual stimulation of the clitoral region. Nevertheless, locating the modulation port at the housing may be less cumbersome, especially for the patient's partner. Alternatively, one or more remote vacuum modulation ports can be provided, operably coupled with the vacuum cup or other applicator of any of the embodiments disclosed herein by e.g. tubing or other mechanism.

Vacuum and/or pressure modulation also can be achieved by incorporating into the pump/motor assembly 300 a variable motor speed feature, or by rapidly rotating air bleed wheel 280 back and forth.

Figure 19:
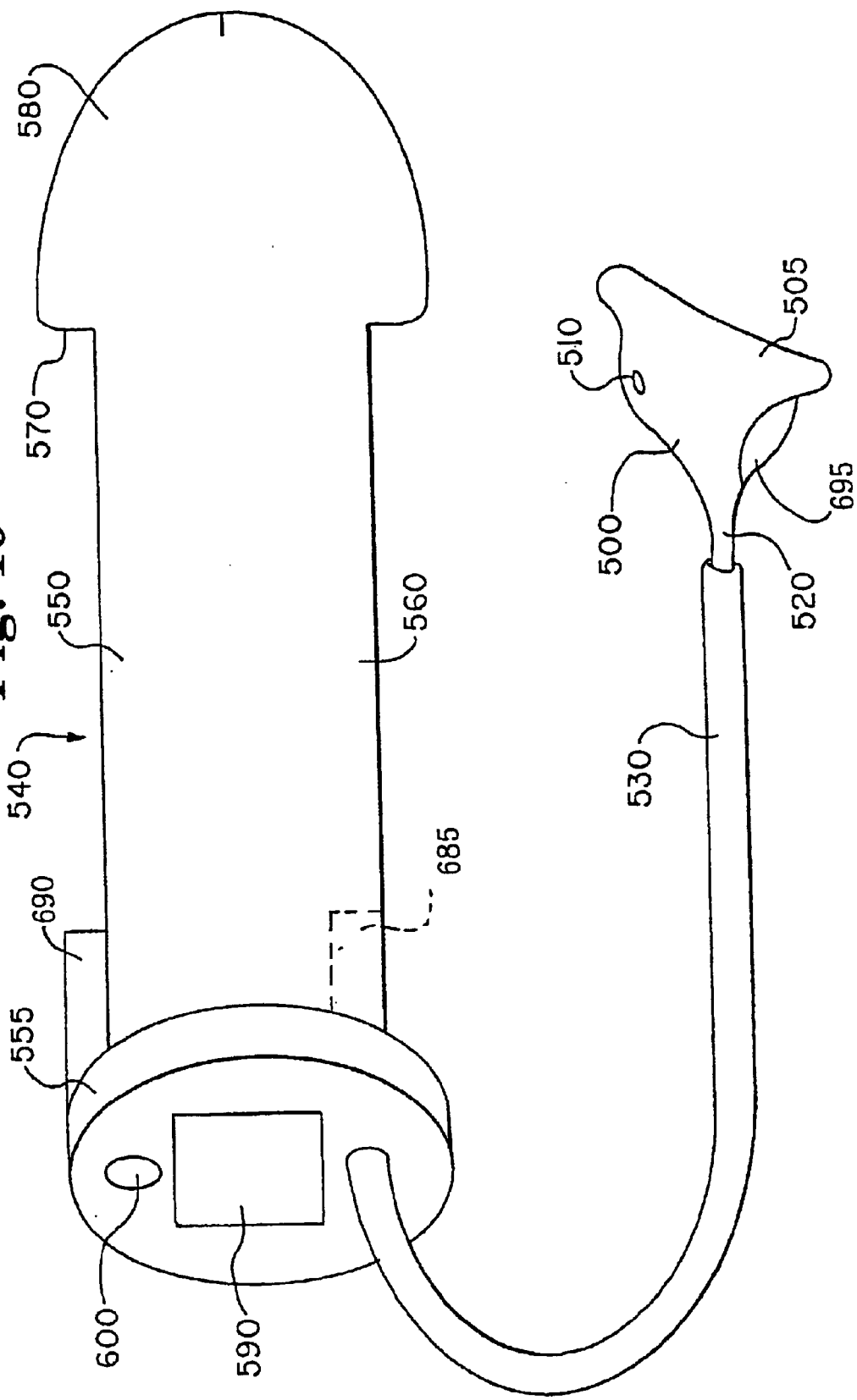
FIG. 19 shows the FIG. 18 vacuum cup in combination with a housing, according to an embodiment of the invention.
Figure 20:
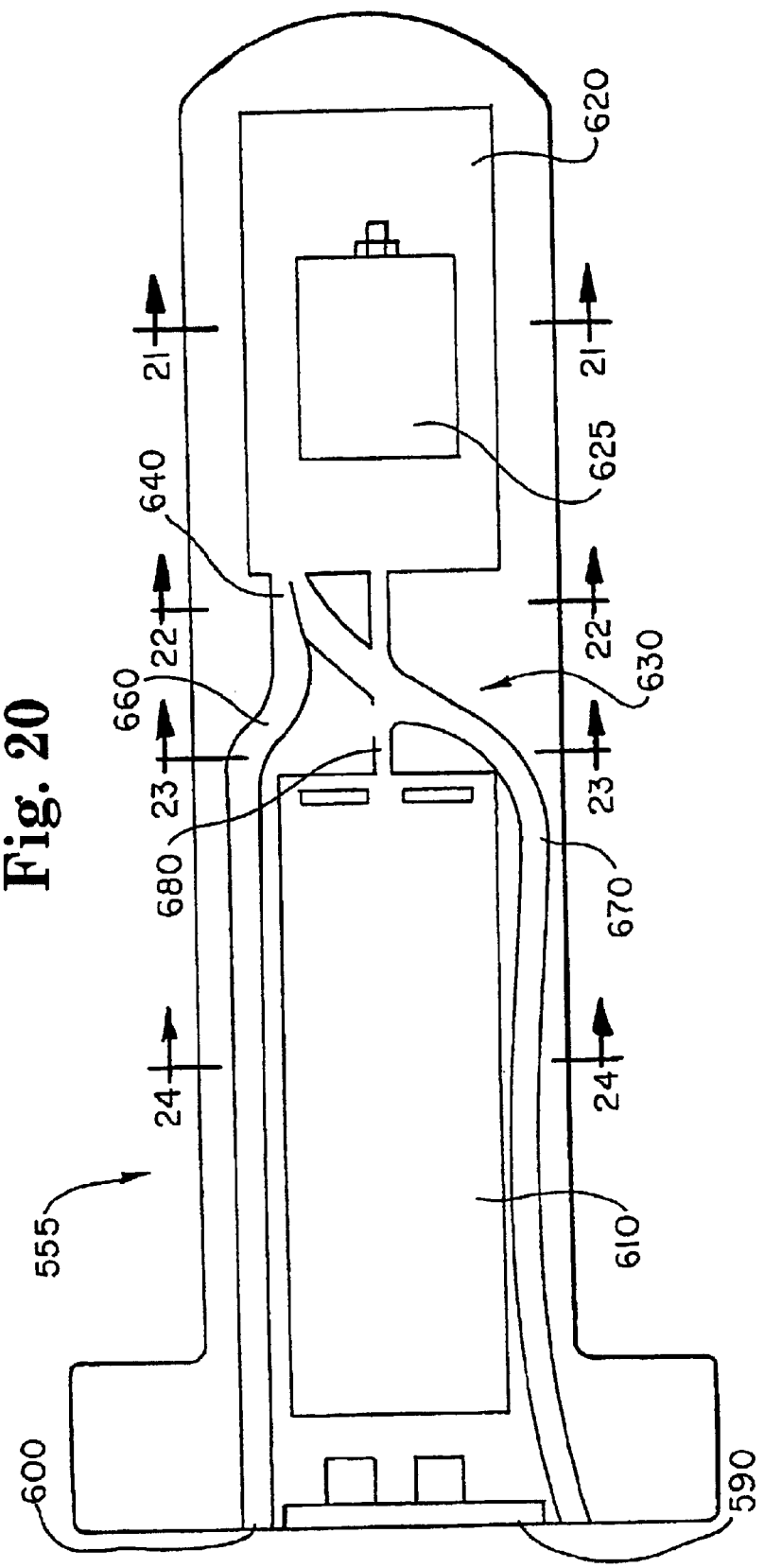
FIG. 20 is a cross-section of an internal portion disposed within the FIG. 19 housing.
Figure 21:
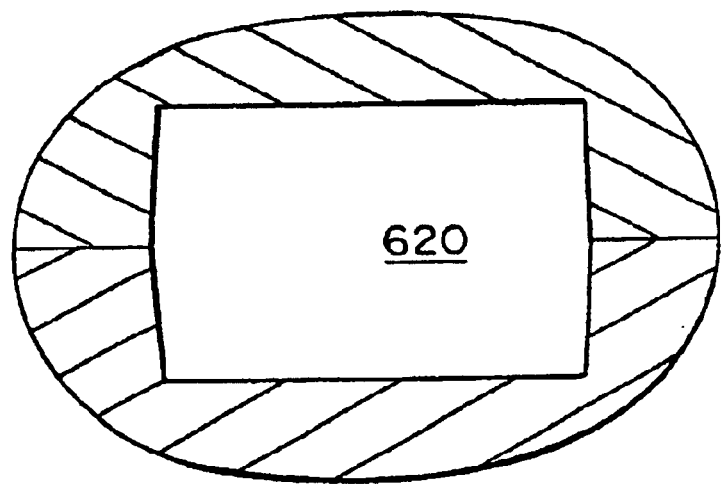
FIG. 21 is a cross-section taken along line 21—21 of FIG. 20.
Figure 22:
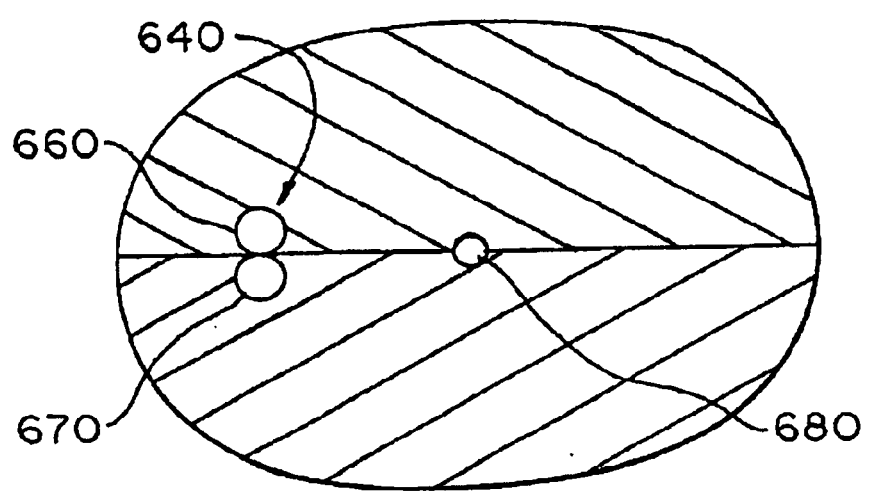
FIG. 22 is a cross-section taken along line 22—22 of FIG. 20.
Figure 23:
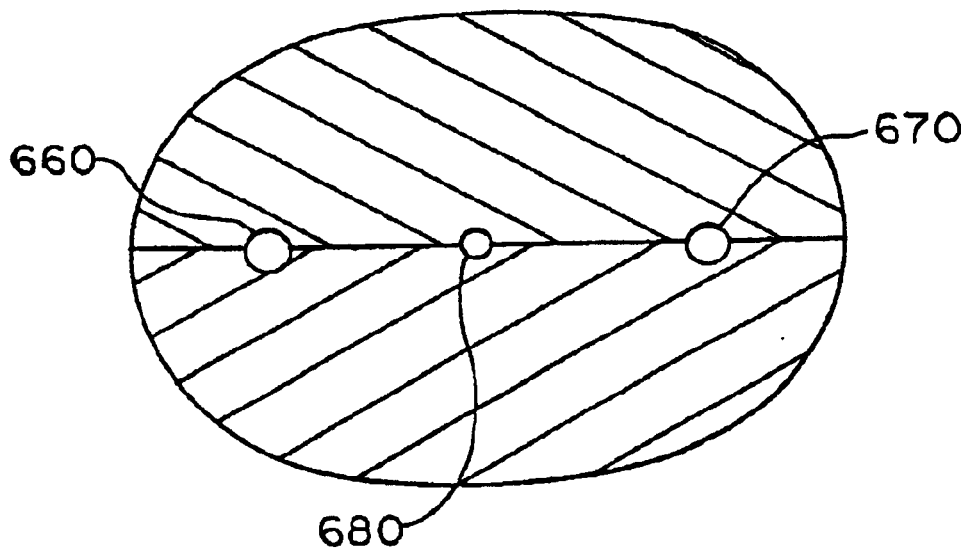
FIG. 23 is a cross-section taken along line 23—23 of FIG. 20.
Figure 24:
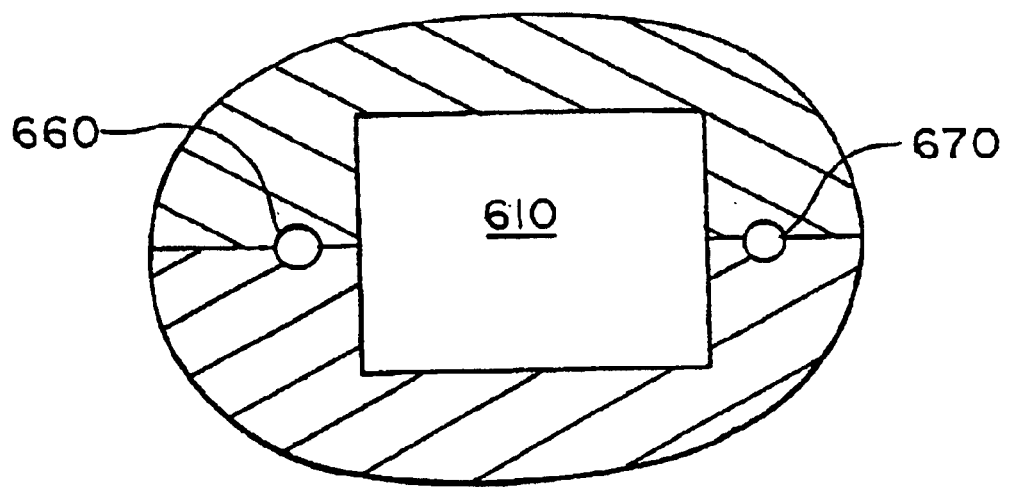
FIG. 24 is a cross-section taken along line 24—24 of FIG. 20.

FIG. 19 also illustrates applicator 500, with vacuum cup 505 attached at neck 520 to vacuum extension tube 530. Extension tube 530 runs between applicator 500 and motor assembly 540 and enhances and simplifies the ability to move and position cup 505 to a desired location. Extension tube 530 is made of the same material as cup 505, according to one embodiment, and can be molded as one-piece therewith or connected as separate pieces.

Motor assembly 540 includes sleeve or cover 550. Sleeve 550 can be in the shape of a penis, with shaft portion 560, glans portion 570 and tip 580. The penis-like shape of sleeve 550 should promote arousal and assist in maintaining clitoral engorgement in certain patients. Additionally, the penis-like shape can be useful in training and/or treating patients who tend to experience urinary and/or fecal incontinence during sexual intercourse. Sleeve 550 also can be used for manual stimulation, e.g. insertion into the vagina, with or without the application of vacuum, in the context of an incontinence-relief training regimen. Sleeve 550 can be formed of a waterproof, biocompatible construction to avoid passage of fluid therethrough, for example in the manner of a condom.

Disposed within sleeve 550 is housing 555, shown in FIGS. 19–24. A portion of housing 555 extends beyond the end of sleeve 550 and includes battery door 590 and exhaust port 600, according to the illustrated embodiment. Battery compartment 610 is disposed immediately behind battery door 590 and includes suitable contacts, springs, etc. for securing e.g. 2 AAA batteries therein. Motor/pump compartment 620 houses a motor/pump assembly, a portion of which is illustrated schematically at 625.

Disposed within and along housing 555 is network 630 of tubes or passages. At portion 640 of network 630, exhaust tube 660 comes into proximity with intake (vacuum) tube 670. Wiring or wire passage 680 connects battery compartment 610 with motor/pump compartment 620. Thus, a vacuum is drawn by the motor/pump assembly via tubes 670, 530 and vacuum cup 505, with air exhausted through exhaust tube 660 and exhaust port 600.

It should be noted that sleeve 550 can be eliminated and housing 555 formed in a substantially penis-like shape or other desired shape more directly. Sleeve 550 minimizes the chances of fouling or contaminating housing 555 with fluid or other foreign matter, however, and so provides certain advantages.

Returning to FIG. 19, applicator 500 (or any of the applicators described in this application) can be used to dispense a topical medication, ointment, lubricant or other such substance to the clitoral or other region, for example in conjunction with the vacuum therapy previously described. Such medication can promote blood flow to the region and/or be intended to alleviate symptoms or address causes of urinary or fecal incontinence. According to one embodiment, the medication or other substance is applied to an interior or exterior surface of cup 505 before patient use. According to other embodiments, a reservoir, either at cup 505 or remote from cup 505, houses the substance. Such reservoirs are illustrated at 685 (internal, remote), 690 (external, remote), and 695 (external, cup) in FIG. 19, although in actual practice only one such reservoir might be preferred. A reservoir lining the interior surface of cup 505 is also contemplated.

The medication or other substance can be dispensed from the reservoir by manually squeezing or compressing the reservoir body, by drawing positive pressure off exhaust port 600 or exhaust tube 660, or in other ways. In the case of a remote reservoir, a supplemental dispensing tube (not shown) can run substantially parallel to and/or be attached to tube 530 to convey the medication or other substance to the interior or exterior of cup 505 or to another desired position for topical application. A reservoir at the interior or exterior of cup 505 likely is the simplest approach, e.g. with a seal being broken to begin dispensing. A reservoir at the cup also would discourage reuse of the cup, promoting cleanliness.

The combination of medicinal and vacuum therapies according to this embodiment should produce a positive synergistic effect in the treatment of urinary and/or fecal incontinence, and/or the promotion and maintenance of clitoral engorgement, in a manner believed heretofore unknown in the prior art. For example, a topical medication for increasing blood flow will be absorbed more quickly, and thus have greater efficacy, if blood flow through and in the clitoris is additionally increased with devices and methods according to the invention.

Additionally, a vibratory effect can be induced in the vacuum cup itself and/or in the motor housing or casing. For example, at least a portion of the cup and/or housing can be provided with or created with a bimorphic piezo material or equivalent, and/or by disposing such material or its equivalent in proximity to the vacuum cup. The piezo material is activated electrically. Alternatively, or additionally, electrical equipment can be used to modulate or pulsate the cup and/or housing. Vibratory effect also can be produced by pneumatic or hydraulic pressure modulation of the cup and/or housing, and/or such modulation of the air within the cup. Because embodiments of the cup are substantially flexible, manually induced vibration also can be accomplished effectively without tissue irritation. Such embodiments also can be used in connection with any or all of the previously described embodiments. In the case of a vibratory housing, housing vibrations are especially well-transmitted to the cup when applicator 500 is of reduced length and/or more directly connected to the housing.

Additionally, a restriction ring, e.g. of elliptical or other shape, can be used to surround and constrict the clitoris, impeding blood outflow, and/or the external urethral orifice, impeding involuntary passage of urine, in connection with embodiments disclosed and discussed in this application. Other cup sizes are contemplated according to embodiments of the invention, large enough to cover the vagina or entire vaginal/labial region, male penile region, or other desired region, as referenced previously.

Figure 25:
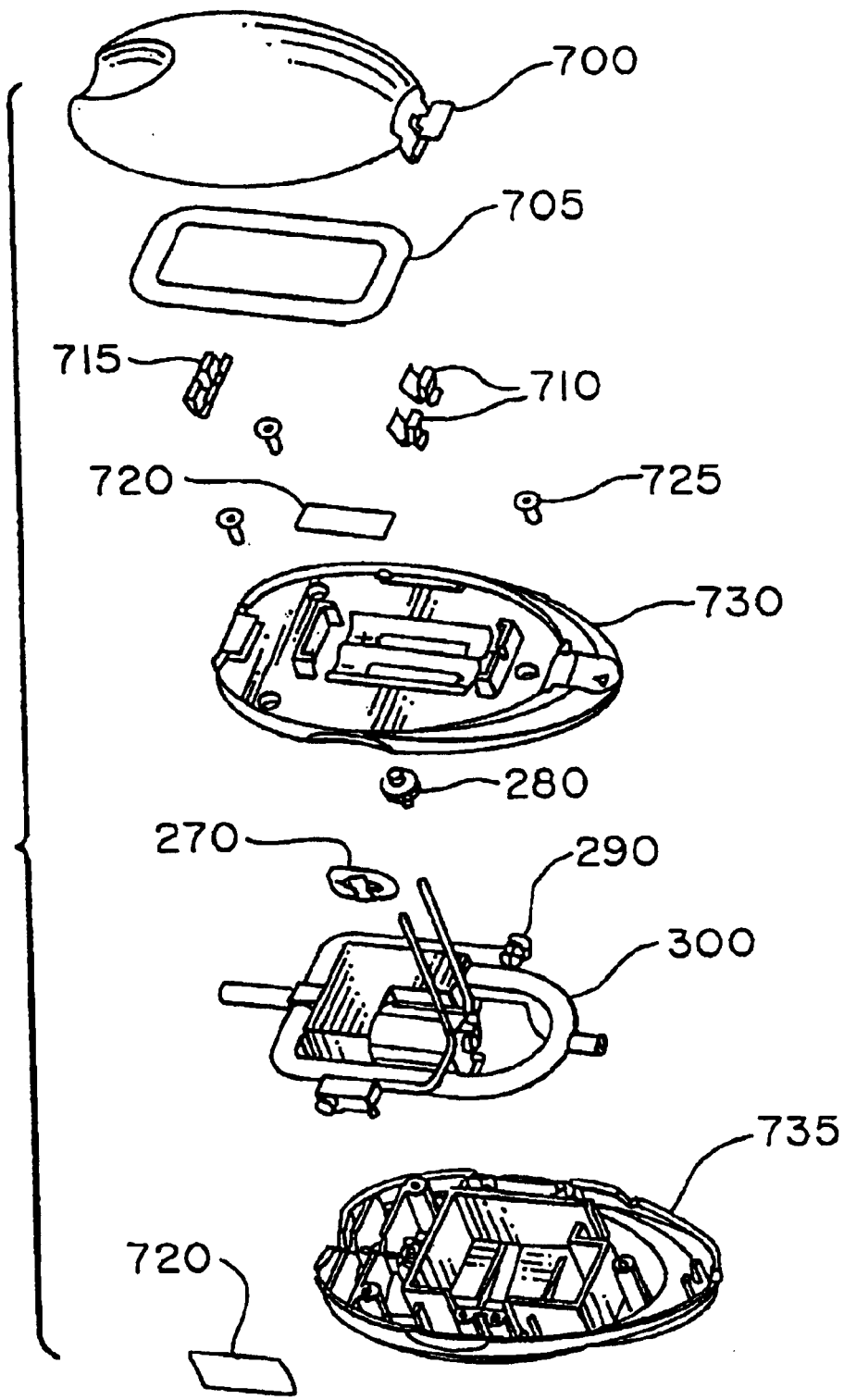
FIG. 25 is an exploded view according to an embodiment of the invention.
Figure 26:
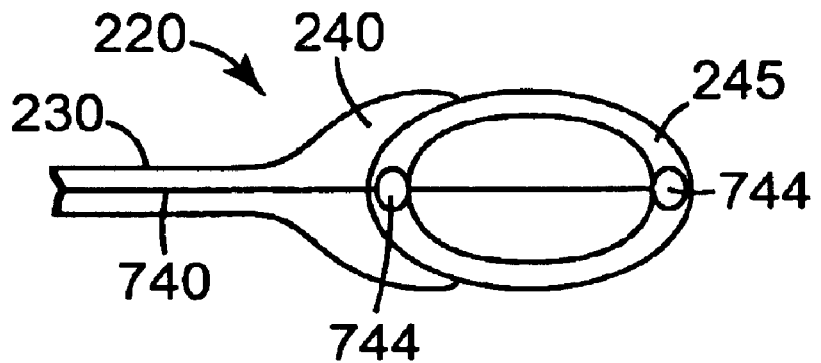
FIG. 26 is a bottom view of a vacuum cup according to an alternative embodiment.
Figure 27:
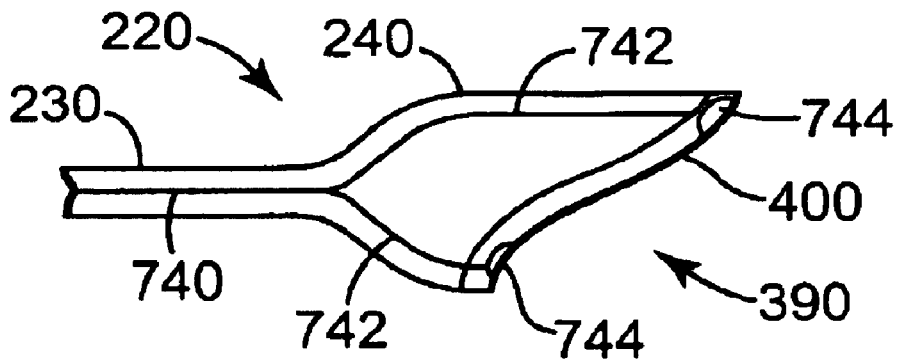
FIG. 27 is a side view of the FIG. 26 vacuum cup.
Figure 28:
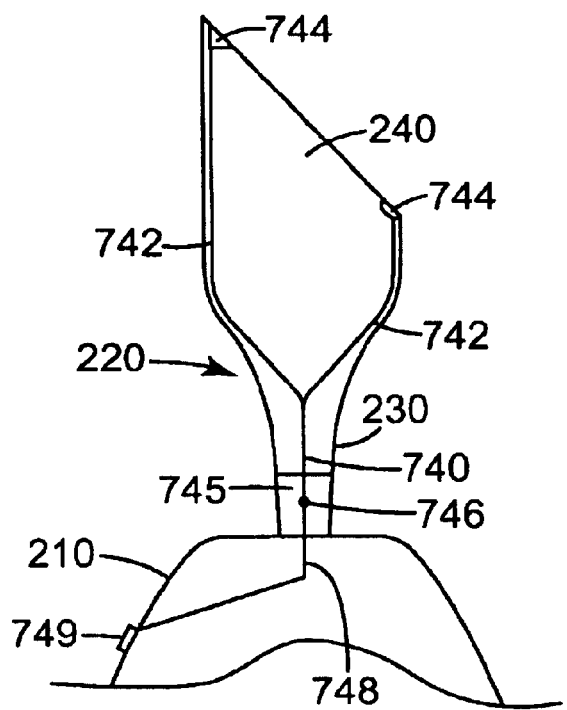
FIG. 28 is a side, partially cut-away view of the FIG. 26 vacuum cup connected to a housing.
Figure 29:
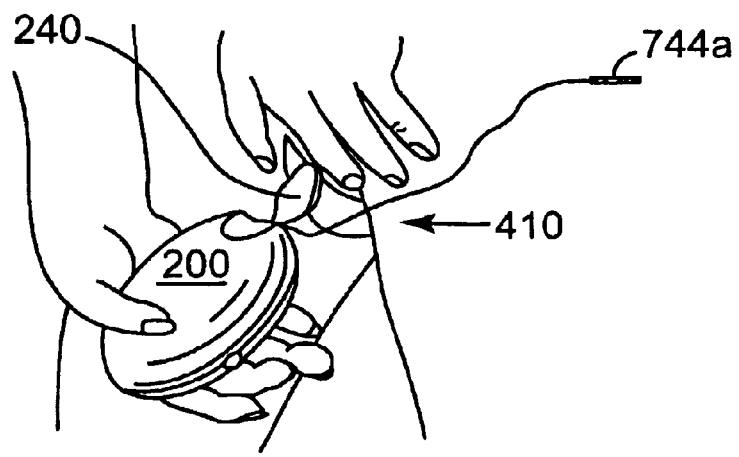
FIG. 29 is a perspective view of an incontinence treatment device in use, according to an embodiment of the invention.

FIG. 25 is an exploded view according to an embodiment of the invention, with many parts thereof already described. Battery cover 700 and battery gasket 705 are disposed over batteries 380 (not shown in FIG. 25), which are secured and electrically contacted by single or double battery terminals 710, 715. Labels 720 can include appropriate written indicia, e.g. one or more company trademarks, patent notices, battery information, consumer or regulatory information, or the like. Fasteners 725, such as flathead screws or the like, secure mid cover 730 in place on base cover 735. Pump/motor assembly 300, modulator or modulation port 290, adjustment wheel 280, and on/off slide switch 270 have been described previously.

FIGS. 26–29 show an alternative embodiment, according to which applicator 220 of device 200 applies electrical stimulation to the clitoris, clitoral region or other region, either alone or in combination or alternation with suction, percussion, or other modulation. Vacuum cup 240 thus is constructed to be an electrical stimulation cup. According to this aspect of the invention, wire, filament or other conductor 740 extends along applicator 220. Conductor 740 extends from a proximal end of neck 230, at or near a point of attachment to casing 210, divides into two branches 742, and terminates in or at contact areas 744. Contact areas 744 are embedded in or disposed at skin-contacting portion 245 of vacuum cup 240. Contact areas 744 are constructed to directly contact the skin of the clitoris or clitoral region, according to this embodiment. Contact areas 744 can be constructed of any suitable material, e.g. biocompatible material, e.g. stainless steel, and can be as small as the diameter of conductor 740 or as large as desired.

According to one embodiment, contact areas 744 can be formed of an electrically conductive vapor-deposited material, such as a noble metal or other metal. Ion beam deposition techniques or other techniques can be used. A wide variety of deposition techniques or other techniques can be used to form or deposit or embed contact areas 744 in or at vacuum cup 240. Additionally, although contact areas 744 are disposed at the base and tip of vacuum cup 240 in FIGS. 26–28, placement on opposite sides of cup 240 or in other locations is also contemplated. More than two contact areas 744, e.g. three, four or eight or more contact areas, can be provided. To produce the best current path across the clitoris, clitoral region or other region, contact areas 744 can be masked off, or otherwise separated, into at least two separate regions. A conductive gel, cream or other substance, such as HYDROGEL, or topical medication, can be placed over or applied to contact areas 744 to improve conductivity, comfort, treatment or other factors. A conductive substance also can itself form contact area(s) 744, with suitable non-conducting barriers or areas between the areas of conductive substance.

The proximal end of neck 230 of vacuum cup 240 is generally hollow and slides over connector 745 (FIG. 28), according to embodiments of the invention, which extends from casing 210. Of course, other connection structures and mechanisms are contemplated and will be apparent to those of ordinary skill. Conductor 740 is connected at coupler 746 to an appropriate electrical conductor or circuitry 748 originating within casing 210 and powered e.g. by the batteries or other power source for device 200. A quick-coupler/quick-disconnect feature is preferred, such that conductors 740, 748 are automatically and easily connected upon attachment of vacuum cup 240 to extension 745 or other portion of device 200. Although conductor 740 can be embedded in applicator 220, it is also contemplated that one or more equivalent conductors can be otherwise attached to or in electrical communication with contact areas 744. Further, connection to the electronics within casing 210 can be at any desired location.

Switch 749, in the form of a push button on the side of casing 210 or other mechanism, can be used to start, stop, and/or modulate or vary the flow of current to contact areas 744 via conductors 740, 748 and coupler 746. Current, voltage, pulse widths, frequency and other parameters can be as used in standard TENS (Transcutaneous Electrical Nerve Stimulation) devices or other nerve stimulation devices. Certain frequencies may be recognized as optimum or preferred depending on the type of incontinence or condition being treated. Electrical stimulation can be used simultaneously with and/or in alternation with vacuum and/or Kegel exercises in the treatment or urinary/fecal incontinence and/or FSAD or erectile dysfunction.

Additionally, one or more electrodes or other electrical contact areas 744a can be placed in contact with another portion or structure of the patient's body, i.e. off cup 240. Doing so can promote better conduction of current along appropriate nerves, for example. According to one embodiment, one or more such additional electrodes or contact areas 744a are placed on the back of the patient, e.g. in the region of the nerve roots S2–S4. Alternatively, rectal, vaginal and/or trans-urethral/bladder electrodes can provide enhanced current flow paths along the appropriate nerves. Such current flow paths can include paths from the clitoris/urethra or clitoral/urethral region to one or more of the anus, back, vagina, bladder or other desired location or area. Each off-cup electrode or area 744a is connected to device 200 e.g. by one or more wires or other conductors, which can be attached to device 200 at a connection point e.g. at or near the connection of cup 240 to device 200. Of course, connection at another portion of device 200 is also contemplated, as is connection to a device that is physically separate but operationally coupled to device 200.

Figure 30:
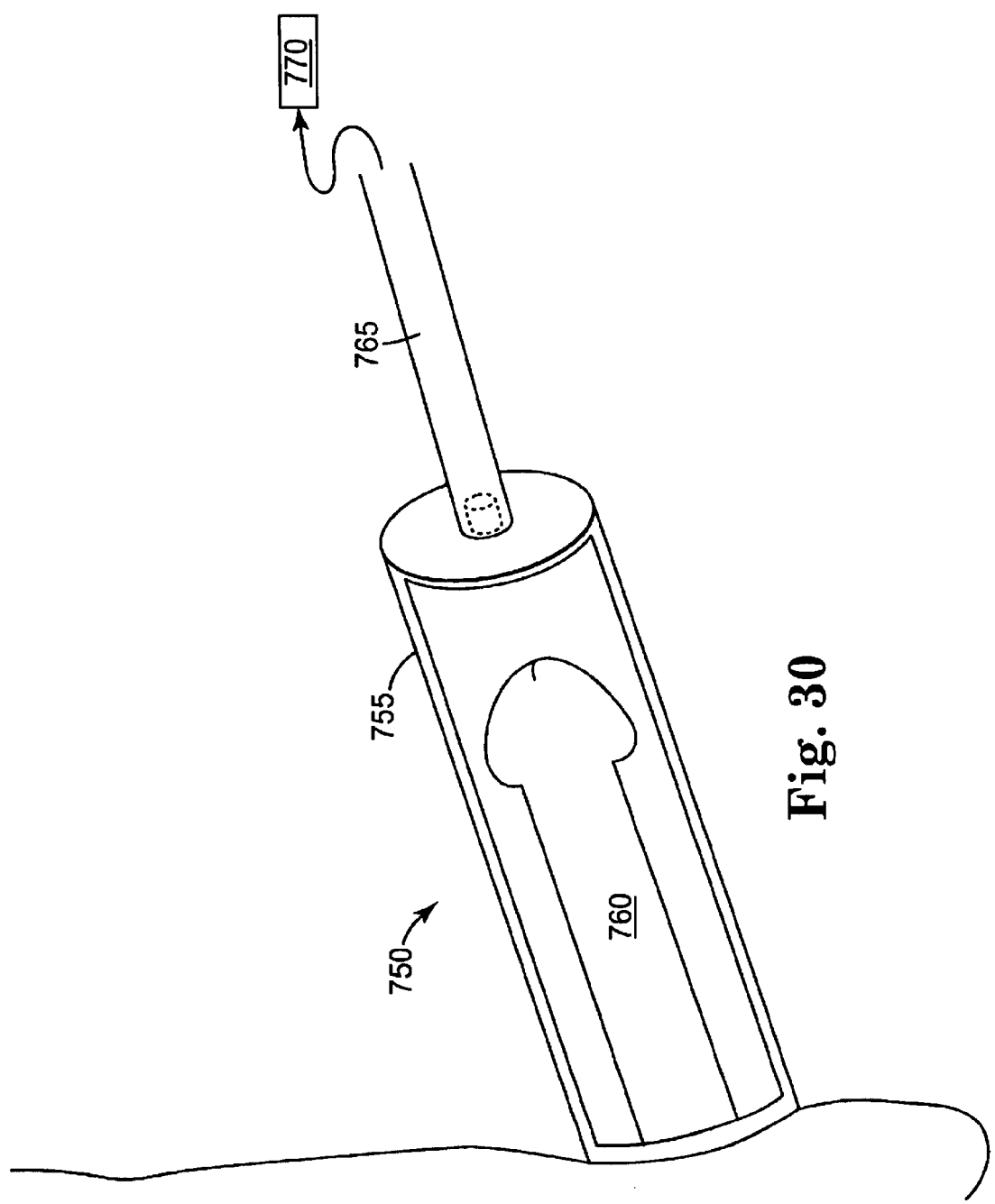
FIG. 30 is a perspective view of a device for treating male incontinence, according to an embodiment of the invention.

FIG. 30 shows device 750 for treating male incontinence of one or more of the above-referenced types. Device 750 includes a generally elongate cylinder 755 for placement over male penis 760. Cylinder 755 creates a substantial vacuum or pressure reduction, via line 765 connected to vacuum source 770. Cylinder 755 thus encourages blood flow into penis 760 and additionally causes nerve and/or nerve root stimulation generally in the manner of previously described embodiments, with corresponding advantages in the treatment of urinary and/or fecal incontinence. The FIG. 30 embodiment also presents advantages in the treatment of male erectile dysfunction, and can be used with or without a constriction band in connection with such treatment.

Diagnostic capabilities for the invention are many. For example, compliance of the clitoris and/or degree to which urinary and/or fecal incontinence is alleviated can be compared to the vacuum level applied, for example to determine the degree of fibrosis and/or to otherwise optimize use of the device and maximize its effectiveness. In combination with ultrasound or other blood flow measuring devices, e.g. either clitoral or vaginal, embodiments of the invention can be used to quantify response characteristics in terms of blood velocity increase. The invention also can be used in combination with vaginal lubricity testing to evaluate reflex response caused by clitoral engorgement. Evaluation of urodymanic pressure transducer profiling can occur, e.g. to analyze modification of pressure profiling due to changes resulting from clitoral or other genital engorgement.

Additionally, vacuum-level variables, time-to-orgasm variables, variables related to the degree to which incontinence is alleviated (e.g. by quantifying the number of occurrences of urine leakage, the amount of urine involuntary passed, and/or amount of time for which relief from incontinence is achieved), and other variables can be determined and compared, from use to use for a single patient and/or from patient to patient, to evaluate proper "dosage" levels—i.e. the amount of time and the level of vacuum to be prescribed for maximum effectiveness. Such levels and variables can facilitate quantitative comparisons between patients to determine the degree of FSAD and/or incontinence. Data can be processed by a microprocessor within the unit, as described above, and/or downloaded to an external microprocessor or other computing device.

Thus, embodiments of the invention apply suction and/or vibration to e.g. the clitoral region or other region of a female patient, or to a male patient, alleviating urinary and/or fecal incontinence and causing or encouraging clitoral engorgement or otherwise alleviating female sexual arousal disorder or male erectile dysfunction. By creating a vacuum over the clitoris, or applying suction to the clitoris or in the clitoral region, a negative pressure is created that is lower than the systolic blood pressure, resulting in engorgement of the clitoris (or, in the male, the penis). If used consistently, embodiments of the invention may reduce the likelihood of fibrosis, at the clitoris and at the urethral sphincter, for example, and consequent reduced clitoral and urethral physiological function.

Additionally, embodiments of the invention likely are restorative to normal physiological clitoral and/or urogenital function. By enhancing and facilitating the removal of collagen from the smooth muscle walls of the clitoris or elsewhere, such embodiments should tend to restore normal blood flow/engorgement, reflex response and physiological function.

Embodiments of the invention also are very small and lightweight, e.g. easily fitting into the palm or otherwise being hand held. As available pump and electronics technology advances, additional size reduction is contemplated if desired.

EXAMPLE

A study of female patients at Boston University, Boston, Mass. and Metropolitan Urological Specialists, St. Paul, Minn. was conducted following approval from the Institutional Review Boards of each center and informed patient consent. The goal of this study was to evaluate the safety and effectiveness of a device according to an embodiment of the invention for enhancing subjective parameters of sexual arousal in women with and without FSAD. These sexual arousal parameters included genital sensation, vaginal lubrication, ability to reach orgasm, and sexual satisfaction. Additionally, patients with complaints of urge incontinence or frequency were evaluated for changes in their bladder control.

A complete medical history and physical examination, including a pelvic examination, was performed on each patient. All menopausal patients had serum estradiol and FSH levels measured and were considered menopausal if they had a lack of spontaneous menstruation for at least 12 months, or estradiol<20 ng and FSH>40 ng. A brief psychosexual history was taken by a sex therapist from all subjects prior to enrollment in the study. Patients who had a history of depression, sexual abuse, hypoactive sexual desire disorder, diabetes, dyspareunia or certain other risk factors were excluded from the study.

Each patient filled out a baseline, pre-treatment Female Intervention Efficacy Index (FIEI), a 5 item questionnaire (Chronbach's Alpha Coefficient 0.81) measuring subjective reports of changes in lubrication, sensation, orgasm, and sexual satisfaction. The FIEI is a validated questionnaire developed by Jennifer Berman, M.D. and Laura Berman, Ph.D.

Following enrollment in the study, a female nurse provided instructions on the use of the device. The patients were shown how to adjust and modulate the vacuum to their individual comfort level. The patients were then asked to practice using the device in the examination room for 5 to 10 minutes. Following this brief session, the female nurse or physician returned to the room to answer any questions and to perform a brief external genital examination.

Patients were asked to use the device in the privacy of their home with or without a partner. During the first three sessions, the patients placed the device over their clitoris and adjusted the vacuum level for an amount of time based on their own satisfaction and arousal. They continued the activation and release of the vacuum over the course of 5–15 minutes. For every home session (1–3) each patient was asked to note any changes in sexual pleasure, including clitoral and labial engorgement, orgasm, and vaginal lubrication on the FIEI. During the next three at-home sessions (4–6) the patients utilized a stopwatch to measure the length of time at which discomfort occurred and to release the vacuum at that time. They were asked to also record the time elapsed until they experienced sexual pleasure and/or orgasm. These times and events were then recorded in a patient diary. Changes in degree of urge incontinence or frequency were also reported.

Weekly phone interviews were held between patients and the principal investigator, nurse, or study coordinator to check on the progress of use, any negative side effects or potential problems.

A second office visit was required at the completion of the six at-home sessions and within 3 months of beginning the study. During this visit, the patient was asked to fill out the FIEI again after using the device for the six sessions to compare baseline and post-treatment responses for each measured aspect of sexual arousal. An external genital examination was performed on each patient. Questionnaires and patient diaries were collected and any questions were answered.

Results

The combined study results of the FIEI questionnaire from 14 patients at both research centers were analyzed. The 14 patients included seven women with complaints of FSAD and seven women with no sexual function complaints. Subjective reports of changes in lubrication, sensation, orgasm, and sexual satisfaction were tabulated for each cohort, and are presented in the table of FIG. 31.

As is evident from FIG. 31, the device was effective in treating symptoms of FSAD including reduced genital sensation, diminished vaginal lubrication, reduced sexual satisfaction, and diminished vaginal lubrication as determined by patient responses on the FIEI self assessment questionnaire. No evidence of clitoral trauma, bruising or irritation was observed during the final physical examination on any of the patients in the study.

FIG. 32 reflects subjective reports of changes in urge incontinence or frequency. Three women that had urge incontinence or frequency problems reported increased bladder control with use of the device. Additionally, after this particular study was completed, these women returned the device and did not use it for six weeks pending FDA clearance. During this time interval they reported that urge incontinence or frequency problems returned. However, resuming use of the device after FDA clearance diminished their incontinence problems, motivating them to use the device long-term.

Additional Data

Figure 33:
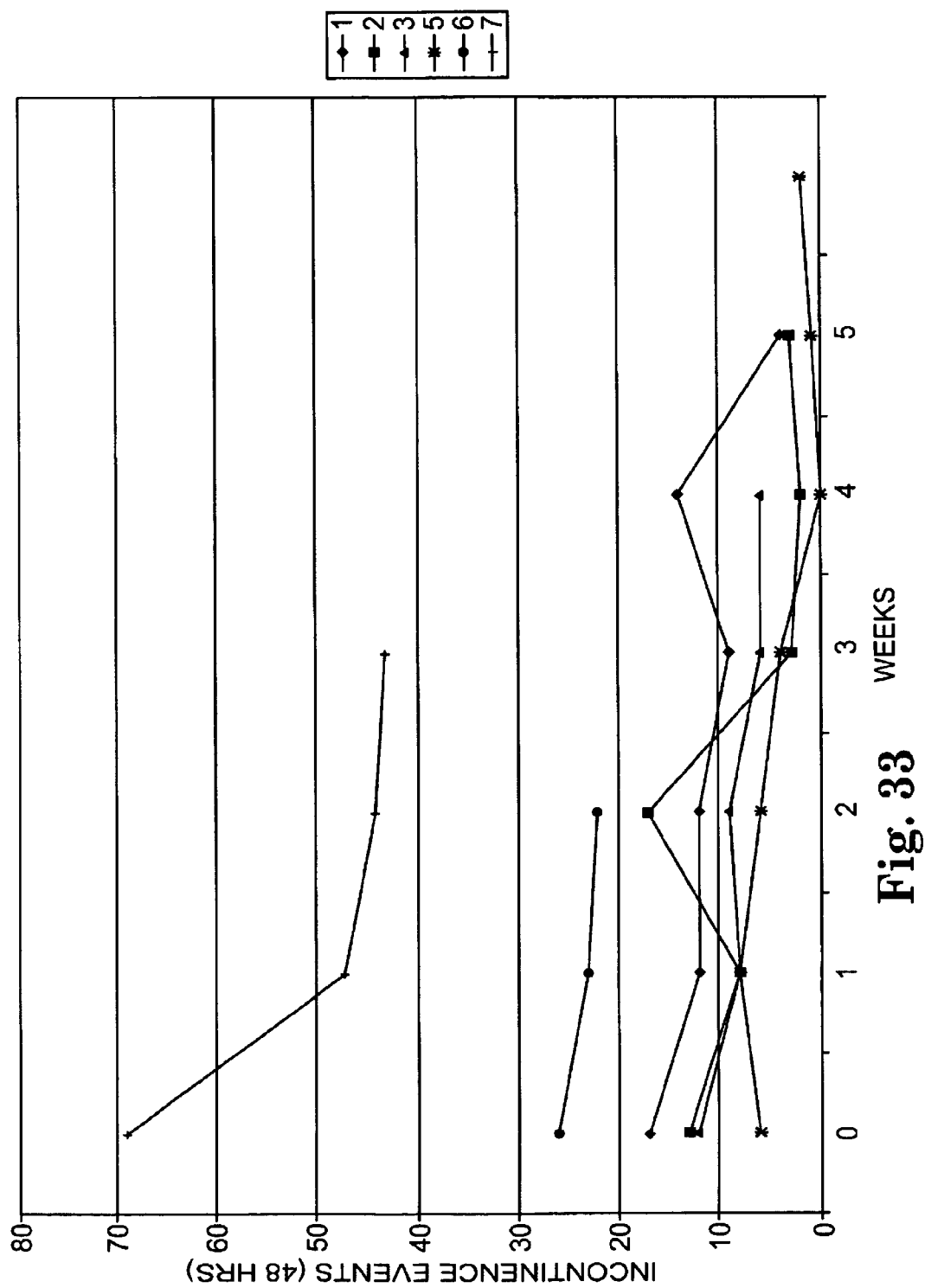
FIG. 33 is a plot reflecting clinical data.
Figure 34:
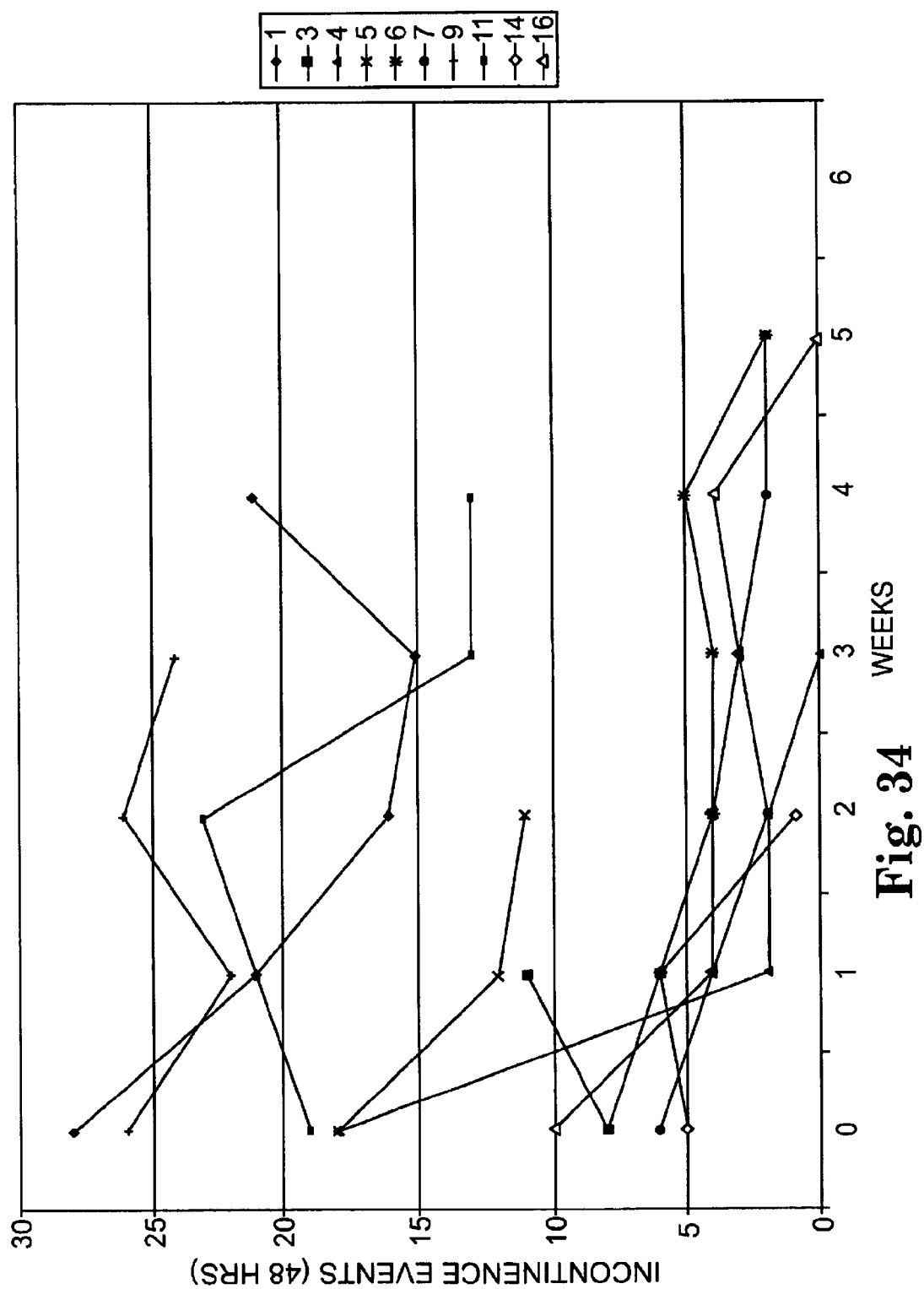
FIG. 34 is an additional plot reflecting clinical data.

FIGS. 33–34 are graphs showing results of several clinical studies in which patients use the vacuum-producing embodiment of the invention illustrated in e.g. FIGS. 4–8. The number of incontinence events (48 hours) is plotted on the y-axis, and the number of weeks of treatment according to embodiments of the invention is plotted on the x-axis. In the great majority of cases, as is evident from the figures, the number of incontinence events declined significantly. More specifically, for the 19 patients reflected in FIGS. 32–34, cure or significant improvement was noted in 12 patients, yielding an efficacy rate of at least 63%. Many of the remaining 7 patients were very close to improvement levels that can be considered significant.

Treatment protocols according to embodiments of the invention can be determined for a particular patient and/or standardized, as needed. According to one example, each patient applies suction to the clitoris or clitoral region 4–5 times per week, at 5–10 minutes per treatment session. In a maintenance mode, patient use can drop to 2–3 times per week. Patients initially can use the device at low vacuum for about 10 seconds to about 90 seconds, for example, and then gradually increase vacuum level and/or treatment times as needed.

Conclusion

While the invention has been described with respect to particular embodiments, the invention is by no means limited to the specific embodiments illustrated and described herein. For example, particular embodiments summarized in e.g. the Summary of the Invention section herein are not intended to be limiting. Embodiments of the invention contemplate creating a substantial vacuum over the clitoris and/or applying a suction force, pressure force, other force and/or electrical stimulation over the clitoris (or, for both, in the clitoral region, urethral region, anal region, vaginal or labial region, male penile region, or other region), and the terms "vacuum" and "suction" should be construed as including one or both concepts, as appropriate. Further, the terms "suction pressure" or "vacuum pressure" should be interpreted as encompassing pressure levels lower than atmospheric or ambient. As referenced earlier, embodiments of the invention also may use pressures higher than ambient or atmospheric, to produce e.g. hydraulic or pneumatic percussion or massage. Portions of the invention described in terms of various embodiments can be used with any other portions—for example, any of the vacuum cup embodiments disclosed herein can be used with any of the housings or casings, modulation and/or application of topical medication can be used with any of the embodiments, aspects described with respect to female-oriented embodiments (e.g. use in conjunction with Kegel exercises) can be used with respect to the male-oriented embodiments, etc. Although embodiments of the invention generally are free of structure constructed to receive and/or accommodate urine from the patient, structure can be added to do so. Various other modifications and changes are readily discernable from the specification and will be apparent to those of ordinary skill.

What is claimed is:

1. A method of treating incontinence in a female patient, the method comprising:

applying a suction, pressure and/or vibratory force to the clitoris, clitoral region, and/or external urethral orifice of the patient to encourage engorgement of the clitoris and/or periurethral tissues;

applying a suction force to reduce intra-clitoral pressure and/or periurethral tissue pressure to a level below the systolic blood pressure of the patient; and physically stimulating at least one nerve to alleviate incontinence in the patient, wherein the applying of suction force occurs simultaneously with patient-directed tightening of pelvic muscles in the patient.

2. A method of treating incontinence in a female patient, the method comprising:

applying a suction, pressure and/or vibratory force to the clitoris, clitoral region, and/or external urethral orifice of the patient to encourage engorgement of the clitoris and/or periurethral tissues;

physically stimulating at least one nerve to alleviate incontinence in the patient;

using an electrical power source to electrically power a device to provide the force, the electrical power source being contained in a hand-sized housing; and applying a suction force to reduce intra-clitoral pressure and/or periurethral tissue pressure to a level below the systolic blood pressure of the patient;

wherein the applying of suction force occurs in alternation with patient-directed tightening of pelvic muscles in the patient.

3. The method of claim 2, wherein the incontinence is alleviated even after suction force is removed.

4. The method of claim 2, wherein physically stimulating the at least one nerve alleviates urinary incontinence in the patient.

5. The method of claim 2, wherein physically stimulating the at least one nerve alleviates fecal incontinence in the patient.

* * * * *